US012763209B2

(12) United States Patent
Liao et al.

(10) Patent No.: US 12,763,209 B2
(45) Date of Patent: Oct. 13, 2026

(54) METHODS AND SYSTEMS FOR DETERMINING ASSESSMENTS OF CARDIOVASCULAR, METABOLIC, AND RENAL SYNDROMES, DISEASES, AND DISORDERS

(71) Applicant: Empallo, Inc., Cambridge, MA (US)

(72) Inventors: Ruizhi Liao, Boston, MA (US); Claire Beskin, Cambridge, MA (US)

(73) Assignee: Empallo, Inc., Cambridge, MA (US)

( * ) Notice: Subject to any disclaimer, the term of this patent is extended or adjusted under 35 U.S.C. 154(b) by 151 days.

(21) Appl. No.: 18/371,284

(22) Filed: Sep. 21, 2023

(65) Prior Publication Data

US 2024/0105336 A1 Mar. 28, 2024

Related U.S. Application Data

(60) Provisional application No. 63/508,312, filed on Jun. 15, 2023, provisional application No. 63/503,945, filed on May 23, 2023, provisional application No. 63/409,107, filed on Sep. 22, 2022.

(51) Int. Cl.

| | |
|---|---|
| ***G16H 50/20*** | (2018.01) |
| ***G16B 20/00*** | (2019.01) |
| ***G16H 50/30*** | (2018.01) |
| ***G16H 50/70*** | (2018.01) |

(52) U.S. Cl.

CPC ............. *G16H 50/20* (2018.01); *G16B 20/00* (2019.02); *G16H 50/30* (2018.01); *G16H 50/70* (2018.01)

(58) Field of Classification Search

CPC ........ G16H 50/20; G16H 50/30; G16H 50/70; G16B 20/00

USPC ............................................................. 705/2

See application file for complete search history.

(56) References Cited

U.S. PATENT DOCUMENTS

2019/0216350 A1* 7/2019 Sullivan ............... A61B 5/7267
2020/0161005 A1* 5/2020 Lyman ................... G16H 15/00
2020/0335220 A1* 10/2020 Snider .................... G16H 50/30
2022/0012309 A1* 1/2022 Shachar ................. G06N 3/084

(Continued)

FOREIGN PATENT DOCUMENTS

JP 2021005325 A * 1/2021

OTHER PUBLICATIONS

Hollenberg, 2019 ACC Expert Consensus Decision Path way on Risk Assessment, Management, and Clinical Trajectory of Patients Hospitalized with Heart Failure: A Report of the American College of Cardiology Solution Set Oversight Committee. Journal of the American College of Cardiology 74(15): 1966-2011 (Year: 2019).*

(Continued)

*Primary Examiner* — Peter H Choi
*Assistant Examiner* — Olivia R. Gedra
(74) *Attorney, Agent, or Firm* — Wiggin and Dana LLP

(57) ABSTRACT

In an aspect, the present disclosure provides a method for determining an assessment of a cardiovascular, metabolic, or renal syndrome, disease, or disorder. The method comprises obtaining a dataset comprising a set of clinical health data of a subject, computer processing the dataset with a trained machine learning algorithm, and based at least in part on the computer processing, determining the assessment of the cardiovascular, metabolic, or renal syndrome, disease, or disorder over a retrospective or future period of time.

23 Claims, 26 Drawing Sheets

(56) References Cited

U.S. PATENT DOCUMENTS

| | | | | |
|---|---|---|---|---|
| 2022/0338828 A1* | 10/2022 | Slomka | ................ | A61B 6/5235 |
| 2024/0082258 A1* | 3/2024 | De Bruin | ........... | A61K 31/4365 |
| 2024/0296959 A1* | 9/2024 | Roberts | .................. | G16H 10/60 |

OTHER PUBLICATIONS

Jang SC. Clinical manifestation, economic burden, and mortality in patients with transthyretin cardiac amyloidosis. Orphanet J Rare Dis. Jul. 15, 2022;17(1):262. doi: 10.1186/s13023-022-02425-3. PMID: 35840997; PMCID: PMC9287852. (Year: 2022).*
Picker, David et al. The number of discharge medications predicts thirty-day hospital readmission: a cohort study.â BMC health services research vol. 15 282. Jul. 23, 2015, doi:10.1186/s12913-015-0950-9 (Year: 2015).*
Yan, et al. Hemoconcentration is a valuable predictor of prognosis in patients with acute heart failure. Experimental and therapeutic medicine vol. 19,4 (2020) (Year: 2020).*
Adams Jr, Kirkwood F, et al., Characteristics and Outcomes of Patients Hospitalized for Heart Failure in the United States: Rationale, Design, and Preliminary Observations from the First 100,000 Cases in the Acute Decompensated Heart Failure National Registry (ADHERE). American Heart Journal 149:209-216 (2005).
Ambrosy, Andrew P, et al., Clinical Course and Predictive Value of Congestion During Hospitalization in Patients Admitted for Worsening Signs and Symptoms of Heart Failure with Reduced Ejection Fraction: Findings from the EVEREST Trial. European Heart Journal 34(11):835-843 (2013).
Benjamin, Emelia J, et al., Heart Disease and Stroke Statistics—2019 Update: A Report from the American Heart Association. Circulation 139(10): e56-e528 (2019).
Cleland, J.G.F, et al., The EuroHeart Failure Survey Programme—A Survey on the Quality of Care Among Patients with Heart Failure in Europe. Part 1: Patient Characteristics and Diagnosis. European Heart Journal 24:442-463 (2003).
Collins, Sean P, et al., Identification of Emergency Department Patients with Acute Heart Failure at Low Risk for 30-day Adverse Events: The STRATIFY Decision Tool. JACC. Heart Failure 3(10):737-747 (2015).
Follath, F, et al., Clinical Presentation, Management and Outcomes in the Acute Heart Failure Global Survey of Standard Treatment (ALARM-HF). Intensive Care Medicine 37(4):619-626 (2011).
Fonarow, Gregg C, et al., Influence of a Performance-improvement Initiative on Quality of Care for Patients Hospitalized with Heart Failure: Results of the Organized Program to Initiate Lifesaving Treatment in Hospitalized Patients with Heart Failure (OPTIMIZE-HF). Archives of Internal Medicine 167(14):1493-502 (2007).
Fonarow, Gregg C, et al., Risk Stratification for in-hospital Mortality in Acutely Decompensated Heart Failure: Classification and Regression Tree Analysis. JAMA 293(5):572-580 (2005).
Greene, Stephen J, et al., Haemoconcentration, Renal Function, and Post-discharge Outcomes Among Patients Hospitalized for Heart Failure with Reduced Ejection Fraction: Insights from the EVEREST Trial. European Journal of Heart Failure 15(12):1401-1411 (2013).
Hollenberg, Steven M, et al., 2019 ACC Expert Consensus Decision Pathway on Risk Assessment, Management, and Clinical Trajectory of Patients Hospitalized with Heart Failure: A Report of the American College of Cardiology Solution Set Oversight Committee. Journal of the American College of Cardiology 74(15):1966-2011 (2019).
Johnson, Alistair E W, et al., MIMIC-IV, A Freely Accessible Electronic Health Record Dataset. Scientific Data 10(1):1-10 (2023).
Kilgore, Meredith, et al., Economic Burden of Hospitalizations of Medicare Beneficiaries with Heart Failure. Risk Management and Healthcare Policy 10:63-70 (2017).
Komajda, M, et al., The EuroHeart Failure Survey Programme—A Survey on the Quality of Care Among Patients with Heart Failure in Europe. Part 2: Treatment. European Heart Journal 24:464-474 (2003).
Krittanawong, Chayakrit, et al., Artificial Intelligence in Precision Cardiovascular Medicine. Journal of the American College of Cardiology 69(21):2657-2664 (2017).
Lesyuk, Wladimir, et al., Cost-of-illness Studies in Heart Failure: A Systematic Review 2004-2016. BMC Cardiovasclar Disorders 18(1):74, 11 Pages (2018).
Maisel, Alan, et al., Primary Results of the Rapid Emergency Department Heart Failure Outpatient Trial (REDHOT) A Multicenter Study of B-type Natriuretic Peptide Levels, Emergency Department Decision Making, and Outcomes in Patients Presenting with Shortness of Breath. Journal of the American College of Cardiology 44(6):1328-1333 (2004).
Nieminen, Markku S, et al., EuroHeart Failure Survey H (EHFS H): A Survey on Hospitalized Acute Heart Failure Patients: Description of Population. Euro Heart Journal 27:2725-2736 (2006).
O'Connor, Christopher M, et al., Predictors of Mortality After Discharge in Patients Hospitalized with Heart Failure: An Analysis from the Organized Program to Initiate Lifesaving Treatment in Hospitalized Patients with Heart Failure (OPTIMIZE-HF). American Heart Journal 156(4):662-673 (2008).
Passantino, Andrea, et al., Predicting Mortality in Patients with Acute Heart Failure: Role of Risk Scores. World Journal of Cardiology 7(12):902-911 (2015).
Peterson, Pamela N, et al., A Validated Risk Score for in-hospital Mortality in Patients with Heart Failure from the American Heart Association get with the Guidelines Program. Circulation: Cardiovascular Quality and Outcomes 3(1):25-32 (2010).
Pocock, Stuart J, et at., Predicting Survival in Heart Failure: A Risk Score Based on 39 372 Patients From 30 Studies. European Heart Journal 34(19):1404-1413 (2013).
Rajpurkar, Pranav, et al., AI in Health and Medicine. Nature Medicine 28(1):31-38 (2022).
Ruizhi, Liao, et al., Predicting in-hospital Clinical Trajectories Using Machine Learning Tn Patients Admitted with Acute Decompensated Heart Failure. Journal of the American College of Cardiology 81(8): suppl A. 1 page (2023).
Testani, Jeffrey M, et al., Potential Effects of Aggressive Decongestion During the Treatment of Decompensated Heart Failure on Renal Function and Survival. Circulation 122(3):265-272 (2010).
Testani, Jeffrey M, et al., Timing of Hemoconcentration During Treatment of Acute Decompensated Heart Failure and Subsequent Survival: Importance of Sustained Decongestion. Journal of the American College of Cardiology 62(6):516-524 (2013).
Van Der Meer, Peter, et al., The Predictive Value of Short-term Changes in Hemoglobin Concentration in Patients Presenting with Acute Decompensated Heart Failure. Journal of the American College of Cardiology 61(19):1973-1981 (2013).
Zhuang, Fuzhen, et al., A Comprehensive Survey on Transfer Learning. Proceedings of the IEEE 109(1):43-76 (2020).

* cited by examiner

*Inputs may include, but are not limited to, patient demographics, medical history, and clinical data. Clinical data could include Electronic Health Record (EHR) data (e.g., clinical notes, demographics, lab values, physical examination information, vital signs) and medical images (e.g., chest x-rays, echocardiograms, MRIs, PYP scans, scintrographs).

*Inputs may include, but are not limited to, patient demographics, medical history, and clinical data. Clinical data could include Electronic Health Record (EHR) data (e.g., clinical notes, demographics, lab values, physical examination information, vital signs) and medical images (e.g., chest x-rays, echocardiograms, MRIs, PYP scans, scintrographs).

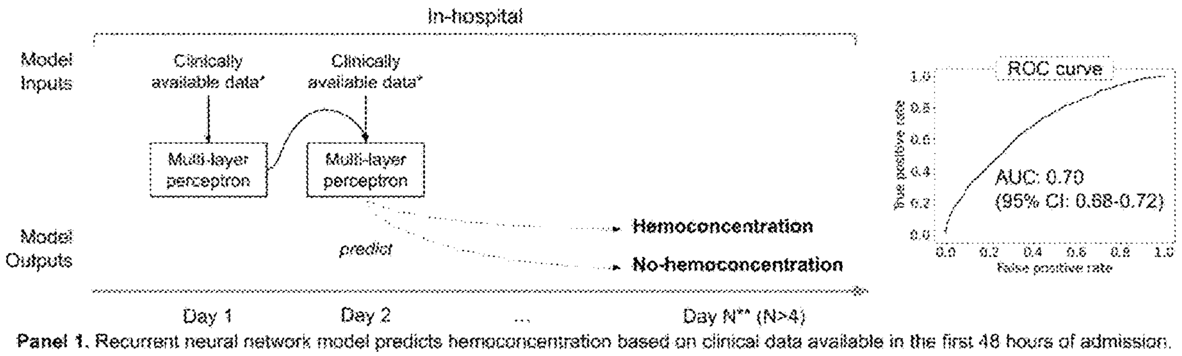

Panel 1. Recurrent neural network model predicts hemoconcentration based on clinical data available in the first 48 hours of admission.

* In this study, the AI model inputs included body weight, comorbidities, demographics, glomerular filtration rate, laboratory tests, vital signs, and diuretic treatment.
** In this cohort of ADHF hospitalizations that have both admission and discharge hemoglobin levels available, the average length of stay is 8.4 days with a standard deviation of 5.0.

| | Overall | AI Predicted Hemo-concentration | AI Predicted No-hemo-concentration | P-Value |
|---|---|---|---|---|
| n | 3,418 | 1,717 (50.2%) | 1,701 (49.8%) | |
| **Mortality, n (%)** | | | | |
| 30-day mortality | 206 (6.0) | 95 (5.5) | 111 (6.5) | 0.25 |
| 6-month mortality | 745 (21.8) | 343 (20.0) | 402 (23.6) | 0.01 |
| 1-year mortality | 1,084 (31.7) | 493 (28.7) | 591 (34.7) | <0.01 |

Panel 2A. AI Predicted Trajectory and Mortality.

| | Overall | Hemo-concentration | No-hemo-concentration | P-Value |
|---|---|---|---|---|
| n | 6,763 | 3,423 (50.6%) | 3,340 (49.4%) | |
| **Mortality, n (%)** | | | | |
| 30-day mortality | 405 (6.0) | 165 (4.8) | 240 (7.2) | <0.01 |
| 6-month mortality | 1,445 (21.4) | 630 (18.4) | 815 (24.4) | <0.01 |
| 1-year mortality | 2,114 (31.3) | 944 (27.6) | 1,170 (35.0) | <0.01 |

Panel 2B. Observed Hemoconcentration and Mortality.

FIG. 25

METHODS AND SYSTEMS FOR DETERMINING ASSESSMENTS OF CARDIOVASCULAR, METABOLIC, AND RENAL SYNDROMES, DISEASES, AND DISORDERS

CROSS-REFERENCE

This application claims the benefit of U.S. Patent Application No. 63/409,107, filed Sep. 22, 2022, U.S. Patent Application No. 63/503,945, filed May 23, 2023, and U.S. Patent Application No. 63/508,312, filed Jun. 15, 2023, each of which is incorporated by reference herein in its entirety.

BACKGROUND

Cardiovascular, metabolic, and renal syndromes, diseases, and disorders may be leading causes of hospitalization, and in-hospital mortality may be high. In-hospital clinical trajectories of admitted patients may be important determinants of post hospital management and prognosis. In particular, early recognition of in-hospital trajectories may be important, especially for those patients not responding to treatment.

SUMMARY

The present disclosure provides methods and systems pertaining to the field of healthcare. In some aspects, the present disclosure provides methods and systems for determining an assessment of a cardiovascular, metabolic, or renal syndrome, disease, or disorder. For example, the methods and systems of the present disclosure may be used for establishing and using a neural network for predicting, assessing, diagnosing, treating, and managing chronic conditions such as heart failure in subjects. The methods and systems of the present disclosure may be performed or used by clinicians or caregivers, such as cardiologists, emergency room (ER) physicians, hospitalists, intensive care unit (ICU) physicians, primary care physicians (PCPs), nurse practitioners (NPs), registered nurses (RNs), physician assistants (PAs), home health and personal care aides, dietitians, nutritionists, personal trainers, fitness coaches, conveners, social workers, and other members of population health management teams.

The present disclosure also provides methods and systems pertaining to the industry of clinical trials. In some aspects, the present disclosure provides methods and systems for optimizing clinical trials according to various parameters, such as eligibility criteria, site selection, subject identification and enrollment. End users may include, but are not limited to, stakeholders from contract research organizations (CROs), medical device manufacturers, and pharmaceutical companies participating in clinical trial design and execution, specifically, but not limited to, those involved in artificial intelligence (AI), machine learning (ML), biostatistics, clinical investigation, clinical science, clinical operations, and medical affairs. End users may also include, but are not limited to, clinicians and other stakeholders participating in identifying and enrolling subjects in clinical trials, such as cardiologists, emergency room (ER) physicians, hospitalists, intensive care unit (ICU) physicians, nurse practitioners (NPs), registered nurses (RNs), physician assistants (PAs), and clinical trial coordinators.

The present disclosure provides methods and systems for determining assessments of various syndromes, diseases, and/or disorders, including, but not limited to, amyloidosis, arrhythmia, atrial fibrillation, diabetes, heart failure, hyperkalemia, hypokalemia, hypertension, hypotension, kidney injury, pulmonary edema, and renal failure. For example, the methods and systems of the present disclosure may predict response to amyloidosis treatments, diuretics, and/or guideline-directed medical therapy (GDMT). The methods and systems of the present disclosure may utilize a combination of subject demographic data, clinical data, and/or other relevant factors to make predictions.

In an aspect, the present disclosure provides a computer-implemented method for determining an assessment of a cardiovascular, metabolic, and/or renal syndrome, disease, and/or disorder. The method may comprise: (a) obtaining a dataset comprising clinical health data of a subject; (b) processing the dataset against a reference or using a trained machine learning algorithm; and (c) based at least in part on the processing in (b), determining the assessment of the cardiovascular, metabolic, or renal syndrome, disease, or disorder over a future period of time.

In some embodiments, determining the assessment of the cardiovascular, metabolic, or renal syndrome, disease, or disorder may comprise determining a response of the subject to a medical treatment. In other embodiments, determining the assessment of the cardiovascular, metabolic, or renal syndrome, disease, or disorder may comprise determining a risk of the subject for having the cardiovascular, metabolic, or renal syndrome, disease, or disorder. In other embodiments, determining the assessment of the cardiovascular, metabolic, or renal syndrome, disease, or disorder may comprise determining a progression or regression of the cardiovascular, metabolic, or renal syndrome, disease, or disorder.

In some embodiments, the subject may have been discharged from a hospital. In other embodiments, the subject may have been initially admitted to a hospital or re-admitted to a hospital for the cardiovascular, metabolic, or renal syndrome, disease, or disorder. In other embodiments, the subject may be treated in an outpatient setting for the cardiovascular, metabolic, or renal syndrome, disease, or disorder. In other embodiments, the subject may be monitored at home for the cardiovascular, metabolic, or renal syndrome, disease, or disorder. In other embodiments, the subject may be a test subject. In other embodiments, the subject may be a part of a clinical trial cohort.

In some embodiments, determining the assessment of the cardiovascular, metabolic, or renal syndrome, disease, or disorder may comprise generating a set of feature importance values of at least a subset of the set of clinical health data. In some embodiments, the method may further comprise generating a visualization of the set of feature importance values. The visualization may comprise information indicative of patient-specific sensitivity analysis (e.g., using feature attribution techniques such as saliency maps, Shapley values, etc.) or population-level sensitivity analysis (e.g., using feature attribution techniques such as one-at-a-time (OAT) analysis and factorial analysis). For example, factorial analysis techniques may account for correlation. The visualization may comprise a saliency map indicative of the set of feature importance values. The saliency map may be individualized for the subject. The saliency map may be generated for each time point among a plurality of distinct time points. Each of the set of feature importance values may be visualized in a row on the saliency map. Each of the set of feature importance values may be represented in different colors on the saliency map. The saliency map may indicate one or more actionable clinical variables from among the set of clinical health data.

In some embodiments, the method may further comprise generating one or more clinical recommendations for the subject, where the one or more clinical recommendations may modify at least one of the one or more actionable clinical variables.

In some embodiments, the set of clinical health data may comprise clinical data of the subject, medical imaging data of the subject, prior clinical history of the subject, personal data of the subject, or a combination thereof. In other embodiments, the clinical data of the subject may comprise diagnosis codes, procedure codes, vital signs, laboratory results, medication history, comorbidities, disease severity indicators, clinical notes, or a combination thereof. The prior clinical history of the subject may comprise prior hospitalizations, emergency department (ED) visits, readmissions, outpatient visits, other relevant healthcare utilization history, or a combination thereof. The personal data of the subject may comprise demographic information of the subject. The demographic information may comprise age, gender, race, ethnicity, socioeconomic status, geographic location, or a combination thereof.

In some embodiments, determining the assessment of the cardiovascular, metabolic, or renal syndrome, disease, or disorder may comprise determining a prediction, a progression, or a regression of a health marker of the subject over the future period of time. The health marker may be selected from the group consisting of B-type natriuretic peptide (BNP), a hemoconcentration marker, creatinine, and a body weight of the subject.

In some embodiments, determining the assessment of the cardiovascular, metabolic, or renal syndrome, disease, or disorder may comprise determining a prediction, a progression, or a regression of an adverse event to the subject over the future period of time. The adverse event may be selected from the group consisting of kidney injury, hypokalemia, mortality, hospital admission, and hospital readmission. The set of clinical health data may comprise one or more symptoms of the subject associated with the adverse event. The one or more symptoms may comprise edema, jugular vein distention (JVD), or rales.

In some embodiments, the medical treatment may comprise a cardiac amyloidosis treatment. In some embodiments, determining the assessment of the cardiovascular, metabolic, or renal syndrome, disease, or disorder may comprise risk stratifying the subject as having transthyretin amyloidosis with cardiac manifestation (ATTR-CM) or not having ATTR-CM. Risk stratifying the subject as having ATTR-CM may comprise determining a predicted mortality of the subject. The mortality may be a two-year mortality. The mortality may be a five-year mortality.

In some embodiments, the method may further comprise generating a visualization of a set of feature importance values of at least a subset of the set of clinical health data, where the set of feature importance values may be associated with the two-year mortality, and where the set of feature importance values may comprise one or more of B-type natriuretic peptide (BNP), a cardiac index, a left ventricular systolic stroke volume index, a presence or an absence of a chronic pulmonary disease of the subject, or an age of the subject.

In some embodiments, the method may further comprise generating a visualization of a set of feature importance values of at least a subset of the set of clinical health data, where the set of feature importance values is associated with the five-year mortality, and wherein the set of feature importance values comprises one or more of B-type natriuretic peptide (BNP), creatinine, a left ventricular systolic stroke volume index, a presence or an absence of a chronic pulmonary disease of the subject, or an age of the subject.

In some embodiments, the medical treatment may comprise a diuretic therapy. In some embodiments, determining the assessment of the cardiovascular, metabolic, or renal syndrome, disease, or disorder may comprise determining a likelihood or probability of decongestion over a future period of time, responsive to the diuretic therapy.

In some embodiments, the method may further comprise selecting the subject to receive the medical treatment, based at least in part on the assessment of the cardiovascular, metabolic, or renal syndrome, disease, or disorder.

In some embodiments, the method may further comprise administering the medical treatment to the subject, based at least in part on the assessment of the cardiovascular, metabolic, or renal syndrome, disease, or disorder.

In some embodiments, the method may further comprise selecting the subject to not receive the medical treatment and to receive an alternative treatment, based at least in part on the assessment of the cardiovascular, metabolic, or renal syndrome, disease, or disorder.

In some embodiments, the trained machine learning algorithm may have a sensitivity of at least about 50%, at least about 55%, at least about 60%, at least about 65%, at least about 70%, at least about 75%, at least about 80%, at least about 85%, at least about 90%, or at least about 95%. In other embodiments, the trained machine learning algorithm may have a specificity of at least about 50%, at least about 55%, at least about 60%, at least about 65%, at least about 70%, at least about 75%, at least about 80%, at least about 85%, at least about 90%, or at least about 95%. In other embodiments, the trained machine learning algorithm may have an accuracy of at least about 50%, at least about 55%, at least about 60%, at least about 65%, at least about 70%, at least about 75%, at least about 80%, at least about 85%, at least about 90%, or at least about 95%. In other embodiments, the trained machine learning algorithm may have a positive predictive value of at least about 50%, at least about 55%, at least about 60%, at least about 65%, at least about 70%, at least about 75%, at least about 80%, at least about 85%, at least about 90%, or at least about 95%. In other embodiments, the trained machine learning algorithm may have a negative predictive value of at least about 50%, at least about 55%, at least about 60%, at least about 65%, at least about 70%, at least about 75%, at least about 80%, at least about 85%, at least about 90%, or at least about 95%.

In some embodiments, the trained machine learning algorithm is selected from the group consisting of a recurrent neural network (RNN) and a convolutional neural network (CNN).

Another aspect of the present disclosure provides a system comprising one or more computer processors and computer memory coupled thereto. The computer memory comprises machine executable code that, upon execution by the one or more computer processors, implements any of the methods above or elsewhere herein.

In an aspect, the present disclosure provides a computer system for determining an assessment of a cardiovascular, metabolic, or renal syndrome, disease, or disorder. The system may comprise a database configured to store a dataset comprising a set of clinical health data of the subject; and one or more computer processors operatively coupled to said database, wherein said one or more computer processors are individually or collectively programmed to (i) process the dataset against a reference or using a trained machine learning algorithm; and (ii) based at least in part on the computer processing in (b), determine the assessment of the cardiovascular, metabolic, or renal syndrome, disease, or disorder over a future period of time.

Another aspect of the present disclosure provides a non-transitory computer-readable medium comprising machine-executable code that, upon execution by one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 25 shows in Panel 1 an example of a recurrent neural network model that predicts hemoconcentration early based on clinical data available in the first 48 hours of hospital admission (e.g., by Day 2 of the hospitalization). Panel 2A shows association of AI-predicted hemoconcentration with out-of-hospital mortality; Panel 2B shows association of observed discharge hemoconcentration with out-of-hospital mortality.

DETAILED DESCRIPTION

Figure 1:
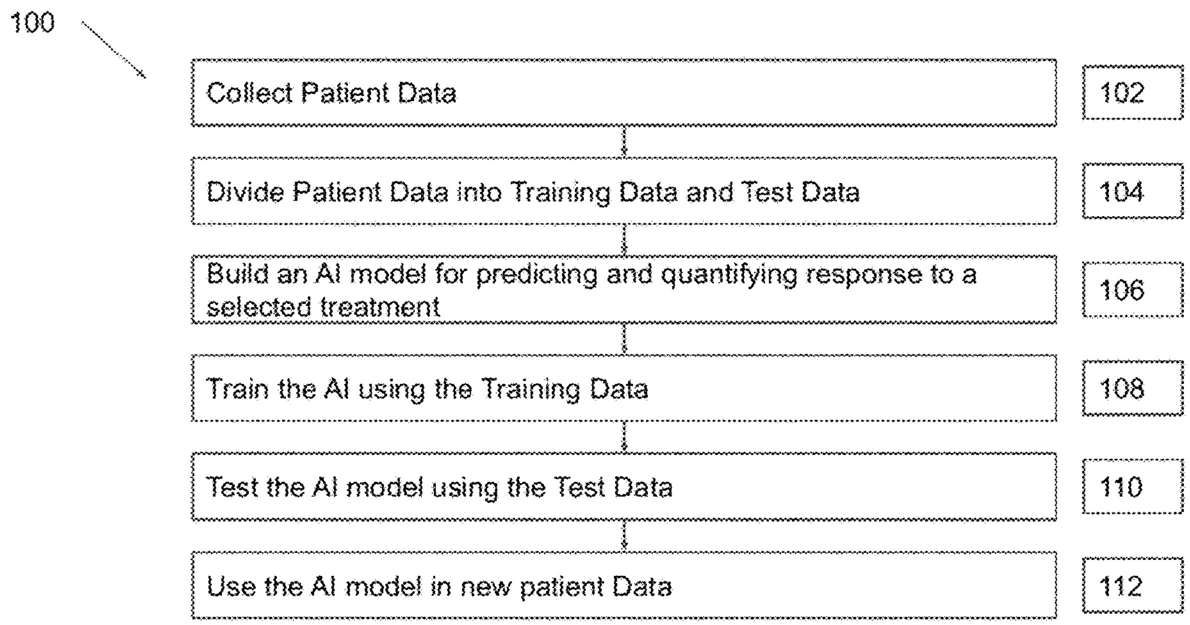
FIG. 1 illustrates an example of a method 100 for using an AI/ML model for predicting and/or quantifying response to a treatment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has a cardiovascular, metabolic, or renal syndrome, disease, or disorder, or a person that is suspected of having a cardiovascular, metabolic, or renal syndrome, disease, or disorder. The subject may be displaying a symptom(s) indicative of a health or physiological state or condition of the subject, such as a cardiovascular, metabolic, or renal syndrome, disease, or disorder. As an alternative, the subject can be asymptomatic with respect to such health or physiological state or condition.

As used herein, the term "sample," generally refers to a biological sample obtained from or derived from one or more subjects. Biological samples may be processed or fractionated. For example, biological samples may include blood, plasma, serum, urine, saliva, tissue, and derivatives thereof. Biological samples may be obtained or derived from subjects using various techniques, such as biopsy or blood collection tubes. Biological samples may be derived from whole blood samples by fractionation. Biological samples or derivatives thereof may contain cells. For example, a biological sample may be a blood sample or a derivative thereof (e.g., blood collected by a collection tube or blood drops).

The present disclosure provides methods and systems pertaining to the field of healthcare. In some aspects, the present disclosure provides methods and systems for determining an assessment of cardiovascular, metabolic and/or renal syndromes, diseases, and/or disorders. The methods and systems of the present disclosure may be performed or used by caregivers, such as cardiologists, emergency room (ER) physicians, hospitalists, intensive care unit (ICU) physicians, nurse practitioners (NPs), registered nurses (RNs), physician assistants (PAs), home health and personal care aides, registered dieticians, nutritionists, personal trainers, fitness coaches, conveners, social workers, or other members of population health management teams.

The present disclosure also provides methods and systems relating to the industry of clinical trials. In some aspects, the methods and systems of the present disclosure may be used to optimize clinical trials according to various parameters, such as eligibility criteria, site selection, and/or subject enrollment. End users may include, but are not limited to, stakeholders from contract research organizations (CROs), medical device manufacturers, and pharmaceutical companies participating in clinical trial design and execution, specifically, but not limited to, those involved in artificial intelligence (AI), machine learning (ML), biostatistics, clinical investigation, clinical science, clinical operations, and medical affairs. End users may also include, but are not limited to, clinicians and other stakeholders participating in identifying and enrolling subjects in clinical trials, such as cardiologists, emergency room (ER) physicians, hospitalists, intensive care unit (ICU) physicians, nurses, physician assistants, and clinical trial coordinators.

The present disclosure provides methods and systems for determining an assessment, for example, predicting and/or quantifying response to treatments for various cardiovascular, metabolic, and/or renal syndromes, diseases, and/or disorders, including, but not limited to, amyloidosis, atrial fibrillation, diabetes, heart failure, hyperkalemia, hypokalemia, hypertension, hypotension, kidney injury, pulmonary edema, and renal failure. For example, the methods and systems may predict response to amyloidosis treatments, diuretics, and/or guideline-directed medical therapy (GDMT). The methods and systems of the present disclosure may utilize a combination of subject demographic data, clinical data, and/or other relevant factors to make predictions.

Methods and systems of the present disclosure may use trained AI/ML models for determining an assessment of a cardiovascular, metabolic, or renal syndrome, disease, or disorder, including predicting and/or quantifying response to treatments. The methods and system of the present disclosure may provide a novel approach to predicting subject outcomes using AI/ML models or other advanced algorithms. For example, by utilizing a subject's demographic information, clinical data, and/or historical data, the model can generate accurate probabilities for mortality, readmission, rehospitalization, and emergency department visits at different time intervals. The use of AI/ML models can improve model accuracy and provide a more detailed understanding of a subject's clinical trajectory. The methods and systems of the present disclosure may be applied to subjects with heart failure, hypertension, atrial fibrillation, amyloidosis, or other cardiovascular, metabolic, or renal syndromes or diseases.

In some embodiments, methods and systems of the present disclosure may use trained AI/ML models for determining an assessment of a cardiovascular, metabolic, or renal syndrome, disease, or disorder. Training of the AI/ML models may comprise various operations including collecting data. Various subject data elements may be collected in the inpatient and/or outpatient environment, which may include but are not limited to a) demographic information such as age, gender, race, ethnicity, socioeconomic status, and geographic location; b) clinical data such as diagnosis codes, procedure codes, vital signs, laboratory results, medication history, comorbidities, disease severity indicators, and clinical notes; c) medical images such as chest x-rays, computed tomography (CT), echocardiograms, magnetic resonance imaging (MRI), and scintigraphy; and d) historical data such as prior hospitalizations, emergency department (ED) visits, readmissions, and relevant healthcare utilization history. A dataset may be divided into training and test cohorts, for example, by randomly assigning 80% of the data to a training cohort and 20% to a testing cohort. The training cohort may be used to train the AI/ML model.

In some embodiments, training of the AI/ML models may comprise building a model, such as a recurrent neural network (RNN) model, to predict and/or quantity response and/or predict risk of adverse reaction to certain treatments, such as amyloidosis medications, diuretics, GDMT, and/or other treatments. Predicting and/or quantifying response may comprise predicting changes in cardiac function, such as predicting changes in ejection fraction (EF), predicting changes in surrogate biomarkers, such as predicting changes in hemoconcentration markers and/or B-type natriuretic peptide (BNP), or predicting changes in a combination thereof, in a subject. For example, such surrogate biomarkers may be measured in a biological sample obtained or derived from the subject. Predicting and/or quantifying risk of adverse reactions may comprise predicting changes in cardiac function, predicting changes in the surrogate biomarkers, such as creatinine and/or potassium, or predicting changes in a combination thereof. For example, such surrogate biomarkers may be measured in a biological sample obtained or derived from the subject. The AI/ML models may be trained on the data from the training cohort, such that the predicted biomarker values are similar to the biomarker values in the training data. For example, a set of parameters may be configured or adjusted such that a loss function is minimized. The test cohort may be used to evaluate model performance. Metrics such as area under the receiver operating characteristic curves (AUC), sensitivity, specificity, positive predictive value, negative predictive value, true positive rate, true negative rate, and/or accuracy may be calculated and used to assess model performance.

The present disclosure provides methods and systems of predicting and/or quantifying response to treatment at intervals that may include, but are not limited to, 1 day, 2 days, 3 days, 4 days, 5 days, 6 days, 7 days, 14 days, 15 days, 30 days, 60 days, 90 days, 6 months, 1 year, 2 years, 3 years, 4 years, 5 years, or 10 years from a reference point in time. The reference point in time may be a particular emergency department (ED) visit, a hospital admission, an outpatient visit, or some other encounter or other point in time.

The present disclosure provides methods and systems of establishing and using AI/ML models for stratifying or phenotyping subjects to predict adverse events and enable personalized interventions. In some embodiments, a method of establishing and using AI/ML models for stratifying or phenotyping subjects to predict adverse events and enable personalized interventions may comprise the steps of preparing clinical data and subject outcomes for artificial neural network development; training a neural network model; and using the trained neural network model to phenotype or stratify subjects to predict clinical trajectories or adverse events.

The first step may comprise preparing clinical data and subject outcomes for artificial neural network development. The first step may further comprise one or more sub-steps, including a) collecting a number of subjects' numerical clinical data, such as vital signs, laboratory tests, medication history, including the values or doses as well as the timestamp of each record; b) if text data is used, collecting the subjects' clinical reports, such as echo reports and radiology reports; c) if image data is used, collecting the subjects' medical images, such as chest radiographs; d) collecting the outcomes of the subjects, such as hospitalization, re-hospitalization, kidney injury, and mortality and trajectories of the subjects, such as BNP values changing over time; and e) generating a unique training data set utilizing the collected data. For example, the unique training data may include inputs such as subject numerical clinical data, radiology reports, and/or radiographs correlated to outputs such as subject outcome. In some embodiments, the unique training data set may be sourced from one or more additional sources such as but not limited to publicly available data, journal articles, expert input, scientific literature, and the like.

The second step may comprise training a neural network model. The second step may further comprise one or more sub-steps, including a) building a neural network model in a server, computer, or any computing device; b) feeding the collected clinical data into the neural network model, where the neural network model may predict the risk or likelihood of adverse events (e.g., inadequate response to treatment, hospitalization, readmission, mortality); and c) adjusting the neural network model parameters by optimizing (e.g., minimizing) the difference between the predicted trajectories or risk and the collected subject trajectories or outcomes.

The third step may comprise using the trained neural network model to phenotype or stratify subjects to predict clinical trajectories or adverse events. The third step may further comprise one or more sub-steps, including given a new subject's clinical data, feeding them into the trained neural network model, where the neural network model may predict the clinical trajectories, and/or the risk or likelihood of adverse events (e.g., inadequate response to treatment, hospitalization, readmission, mortality) of the subject.

The present disclosure provides methods and systems of applying data query and AI/ML solutions to support clinical trials, such as cardiovascular clinical trials, including optimizing site selection, eligibility criteria, and subject identification as well as enrollment. In some embodiments, a method of applying data query and AI/ML solutions to support clinical trials may comprise three steps, including preparing retrospective clinical data and subject outcomes for data query technology and artificial neural network development; training a neural network model; and using the trained neural network model to assess risk of certain events (e.g., inadequate response to treatment, hospitalization, readmission, mortality).

The first step may comprise preparing retrospective clinical data and subject outcomes for data query technology and artificial neural network development. The first step may further comprise one or more sub-steps, including a) collecting a number of subjects' numerical clinical data, such as vital signs, laboratory tests, medication history, including the values or doses as well as the timestamp of each record; b) if text data is used, collecting the subjects' clinical reports, such as echo reports and radiology reports; c) if image data is used, collecting the subjects' medical images, such as chest radiographs; d) collecting the outcomes (events) of the subjects (e.g., hospitalization, readmission, mortality); and e) generating a unique training data set utilizing the collected data. For example, the unique training data may include inputs such as subject numerical clinical data, radiology reports, and/or radiographs correlated to outputs such as subject outcome. In some embodiments, the unique training data set may be sourced from one or more additional sources such as but not limited to publicly available data, journal articles, expert input, scientific literature, and the like.

The second step may comprise training a neural network model. The second step may further comprise one or more sub-steps including a) building a neural network model in a server, computer, or any computing device; b) feeding the collected clinical data into the neural network model, where the neural network model may predict the risk or likelihood of events (e.g., inadequate response to treatment, hospitalization, readmission, mortality) given those subjects' data; and c) adjusting the neural network model parameters by optimizing (e.g., minimizing) the difference between the predicted risk and the collected subject outcomes.

The third step may comprise using the trained neural network model to assess risk of certain events (e.g., inadequate response to treatment, hospitalization, readmission, mortality). The third step may further comprise one or more sub-steps including given a new subject's clinical data, feeding them into the trained neural network model, where the neural network model may predict the risk of certain events (e.g., inadequate response to treatment, hospitalization, readmission, mortality) and/or other outcomes of the new subject.

In some embodiments, the risk predicted by our neural network model is based on the temporal trends and features of the input clinical data (e.g., the change in the clinical data from day one to day two) as well as the features of the most recent clinical data before discharging a patient. The risk assessment may be applied on a patient and the numerical score given by the assessment model indicates how likely this patient is to have an event in the future (such as kidney injury, re-hospitalization, or death).

The systems and methods as described herein may have a variety of benefits to the field of healthcare. The systems and methods can be used to improve subject outcomes. By identifying high-risk subjects early on, healthcare providers can intervene and provide appropriate care to prevent adverse events such as mortality, readmission, rehospitalization, and ED visits. This can lead to improved subject outcomes and a better quality of life for subjects. Further, healthcare costs can be reduced. By preventing adverse events such as readmissions and rehospitalizations, the methods and systems of the present disclosure can help reduce healthcare costs. Hospital readmissions and rehospitalizations are costly, and by preventing them, healthcare providers can save on costs associated with these events. Further, healthcare resources can be better utilized. By identifying high-risk subjects early on, healthcare providers can allocate resources more efficiently. This can lead to more effective use of healthcare resources. Patient engagement can be enhanced. The systems and methods as described herein can help enhance patient engagement by empowering patients to take an active role in their healthcare. Patients who are aware of their risk factors may be more likely to take steps to manage their health and adhere to treatment plans. Moreover, the systems and methods as described herein can improve population health. By preventing adverse outcomes or events such as readmissions and rehospitalizations, the methods and systems of the present disclosure can also contribute to improving the overall health of the population. By reducing the burden on the healthcare system, resources can be redirected towards preventative measures that can benefit the entire population.

FIG. 1 illustrates an example of a method 100 for using an AI/ML model for determining an assessment of various syndromes, diseases, and/or disorders. As illustrated, subject data is collected (step 102) and divided into training data and test data (step 104). An AI/ML model can be built for determining an assessment of various syndromes, diseases, and/or disorders, for example, predicting and quantifying response to a selected treatment (step 106). The AI/ML model can be trained using the training data (step 108), and tested using the test data (step 110). The trained AI/ML model can be used to evaluate new subject data to determine an assessment of various syndromes, diseases, and/or disorders of the new subject (step 112).

Figure 2:
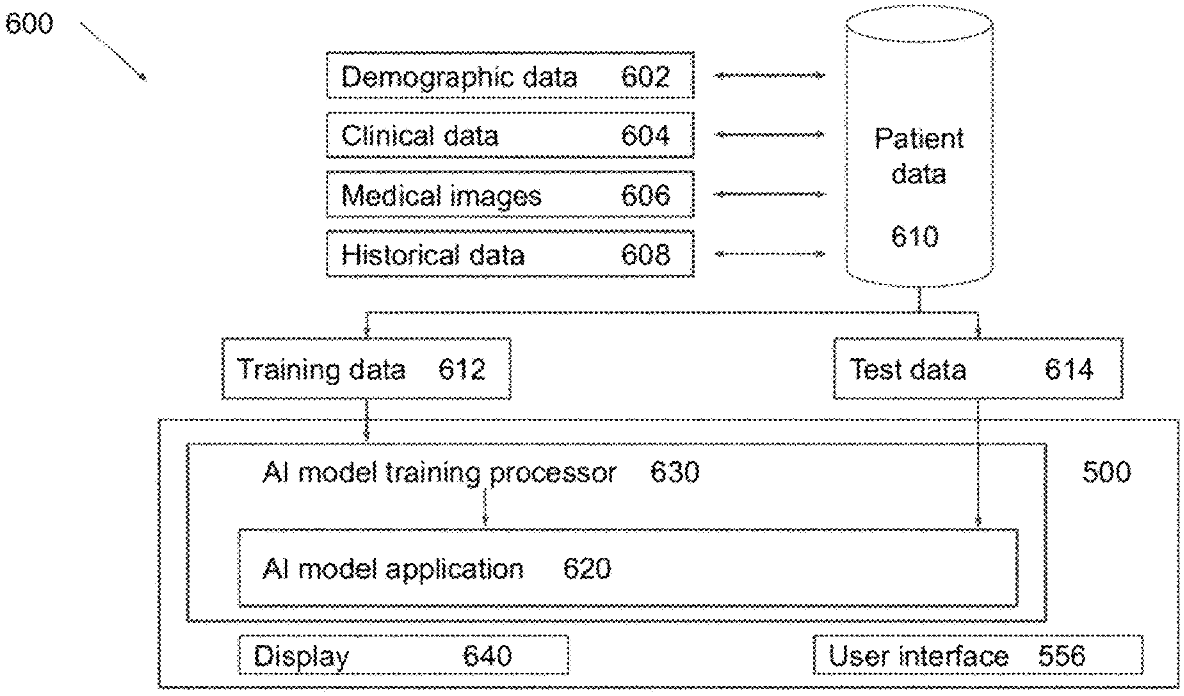
FIG. 2 illustrates an example of a computer system 600 for using an AI/ML model for predicting and/or quantifying response to a treatment.

FIG. 2 illustrates an example of a computer system 600 for using an AI/ML model for predicting and/or quantifying response to a treatment. As illustrated, subject data 610 can be collected, comprising demographic data 602, clinical data 604, medical images 606, and historical data 608. The subject data 610 can be divided into training data 612 and test data 614. Both the training data 612 and test data 614 can be fed to an AI/ML model. As illustrated, the AI/ML model training processor 630 can implement the AI/ML model application 620 in the computing device 500 with display 640 and user interface 556. The AI/ML model can be trained by the training data 612. The trained model can be used to evaluate new subject data to determine an assessment of various syndromes, diseases, and/or disorders of the new subject.

Figure 3:
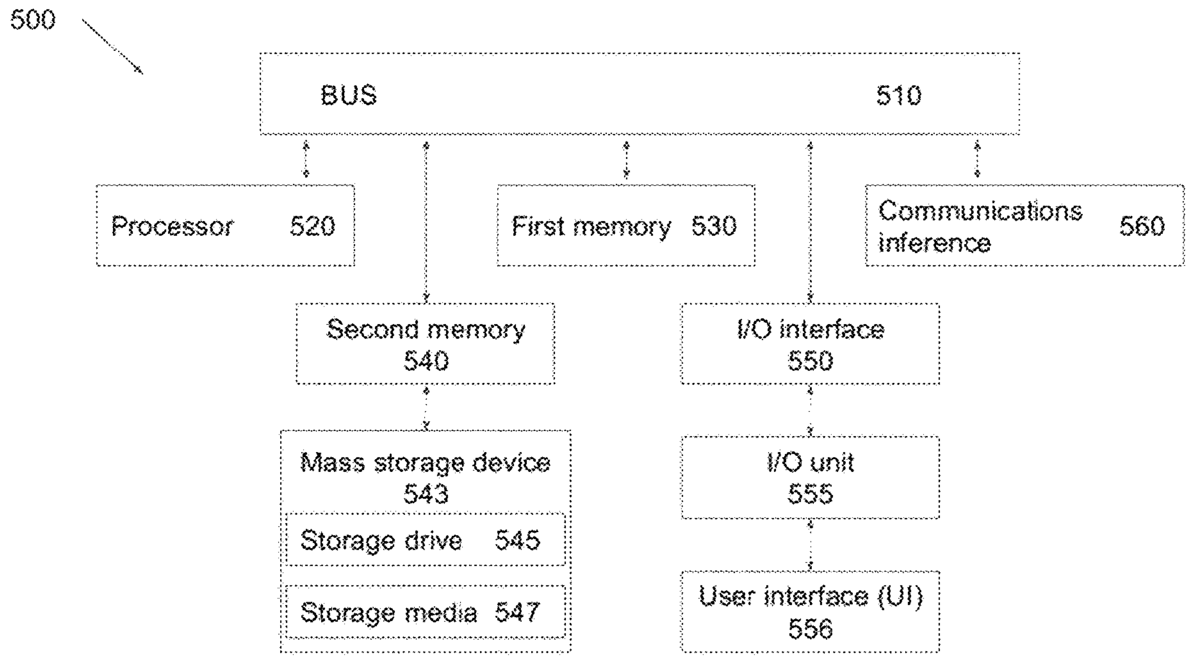
FIG. 3 illustrates another example of a computer system 500 for using an AI/ML model for predicting and/or quantifying response to a treatment.

FIG. 3 illustrates another example of a computer system 500 for using an AI/ML model for predicting and/or quantifying response to a treatment. The computer system 500 comprises one or more processors 520, first memory 530, second memory 540, I/O interface 550, and communications interface 560, each of which is communicatively coupled via BUS 510. The second memory 540 can be communicatively coupled to a mass storage device 543 comprising a storage drive 545 and storage media 547. The I/O interface 550 can be communicatively coupled to I/O unit 555 and user interface (UI) 556.

Figure 4A:
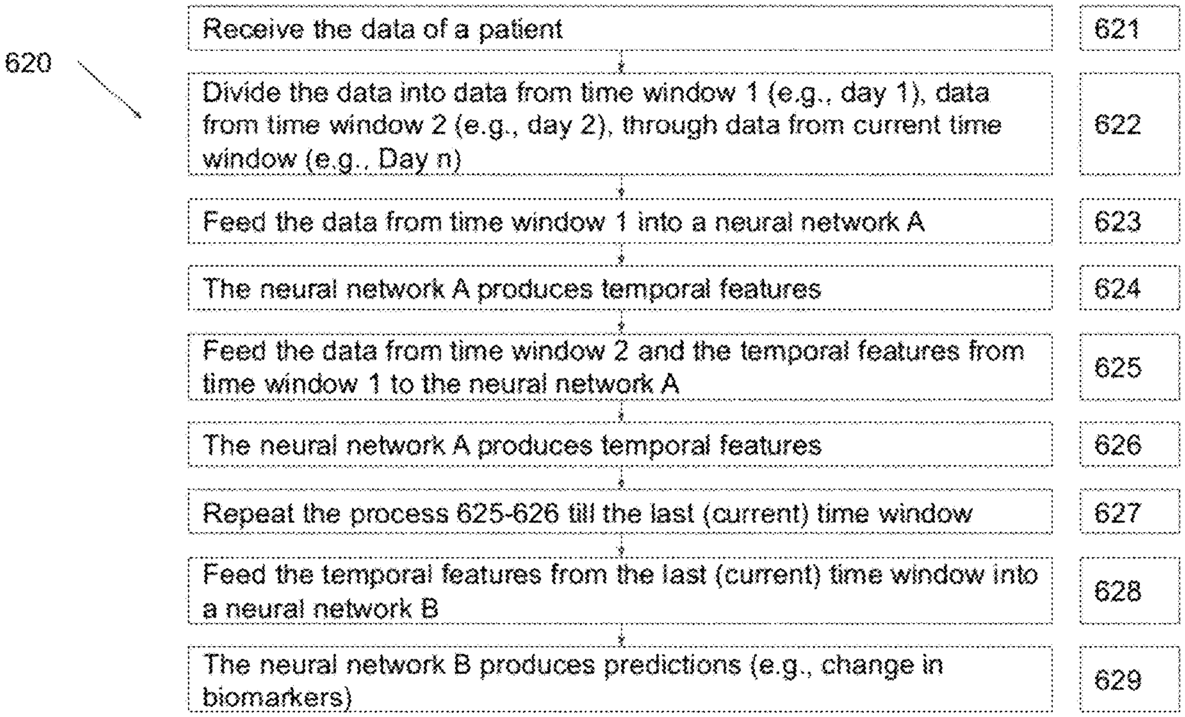
FIG. 4A illustrates an example of AWL module 620 (e.g., an AI/ML model application) for using a neural network to produce predictions (e.g., change in biomarkers).

FIG. 4A illustrates an example of an AI/ML module 620 (e.g., an AI/ML model application) for using a neural network to produce predictions (e.g., change in biomarkers, change in cardiac function). subject data can be received (621) and divided into data segments including data from time window 1 (e.g., day 1), data from time window 2 (e.g., day 2), through data from current time window (e.g., day n) (622). The data from time window 1 can be fed into neural network A, which produces respective temporal features (623 and 624). The data from time window 2 and temporal features corresponding to time window 1 can be fed into neural network A, which produces respective temporal features (624 and 626). These steps (i.e., 625 and 626) can be repeated until the last (current) time window (627). The temporal features corresponding to the last (current) time window can be fed into neural network B, which generates predictions, for example, change in biomarkers (628 and 629).

Figure 4B:
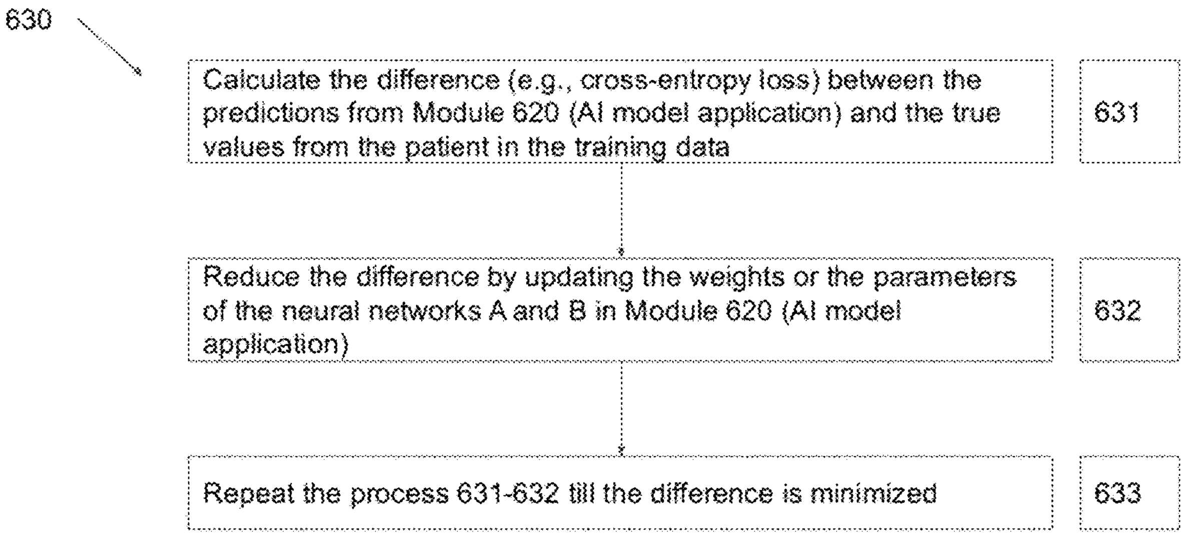
FIG. 4B illustrates an example of a method 630 for training a neural network of AI/ML module 620.

FIG. 4B illustrates an example of a method 630 for training a neural network of AI/ML module. When training data is fed to the AI/ML module, the difference (e.g., cross-entropy loss) between the prediction generated from the AI/ML module 620 (e.g., AI/ML model application) and true values from the subject in the training data can be calculated (631). The difference can be reduced by updating the weights or parameters of the neural networks (e.g., neural networks A and B in FIG. 4A) in the AI/ML module (632). The steps of calculating and reducing the difference (631 and 632) can be repeated until the difference is minimized (633).

Figure 5:
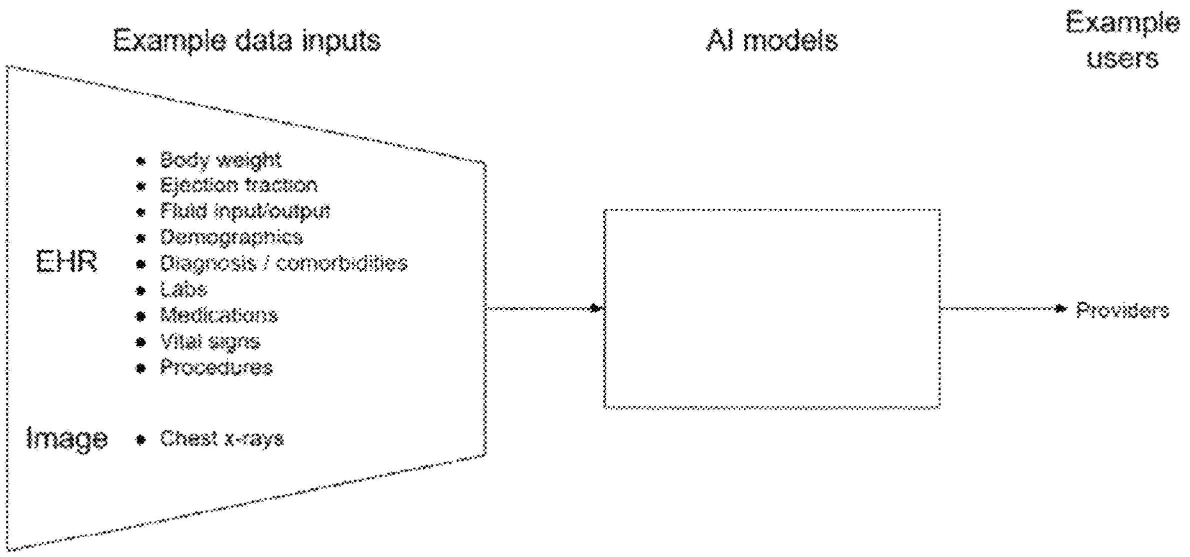
FIG. 5 illustrates an example of using AI/ML models to process subject data and determine an assessment of various syndromes, diseases, and/or disorders.

FIG. 5 shows an example of using AI/ML models to process subject data and determine an assessment of various syndromes, diseases, and/or disorders. Subject data including but is not limited to Electronic Health Record (EHR) data and medical images are fed into the AI/ML models, which analyze the data. Model results are displayed to users such as healthcare providers or clinical trial designers. As illustrated, subject data, including but not limited to Electronic Health Record (EHR) data (e.g., body weight, ejection fraction, fluid input/output, demographics, diagnosis/comorbidities, labs, medications, vital signs, procedures) and medical images (e.g., chest radiographs) are fed into algorithms, such as recurrent neural network (RNN) algorithms, which analyze the data. Model results are displayed to users such as healthcare providers or clinical trial designers.

Figure 6:
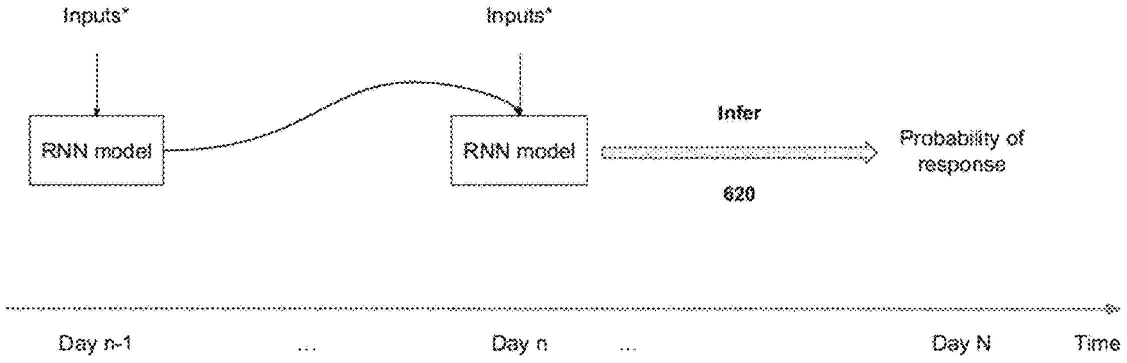
FIG. 6 illustrates an example of a recurrent neural network (RNN) model configured to receive inputs over time (e.g., on each of a plurality of days) and infer a probability of response to a treatment.

FIG. 6 illustrates an example of a recurrent neural network (RNN) model configured to receive inputs over time (e.g., on each of a plurality of days) and infer a probability of response to a treatment. The inputs that are fed to the RNN model include, but are not limited to, subject demographics, medical history, and clinical data. Clinical data include Electronic Health Record (EHR) data (e.g., clinical notes, demographics, lab values, physical examination information, vital signs) and medical images (e.g., chest x-rays, echocardiograms, MRIs, pyrophosphate scintigraphy (PYP) scans, and other scintigraphy).

Figure 7:
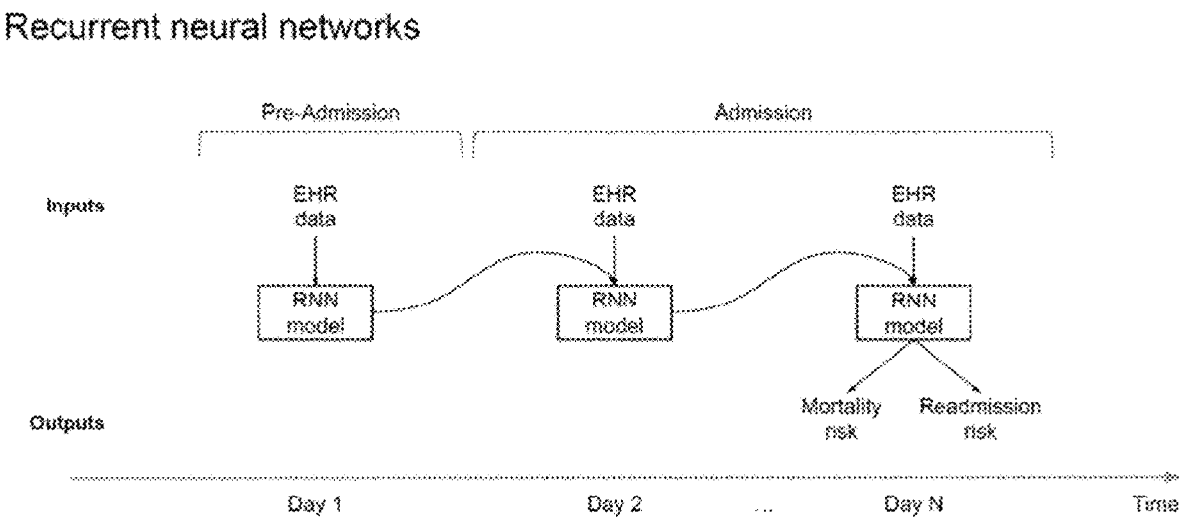
FIG. 7 illustrates another example of a RNN model configured to learn from millions of patient records, capture subtle indicators in temporal trends and multimodal data, and predict patient trajectories.

FIG. 7 illustrates another example of RNN model configured to learn from millions of patient records, capture subtle indicators in temporal trends & multimodal data, and predict subject trajectories. The input to the AI/ML model (e.g., RNN model) includes patients' HER data from preadmission period to admission period. The AI/ML model can predict and output the mortality risk and readmission risk of the patient.

The systems and methods as described herein may predict the risk of certain outcomes or other events for patients with cardiovascular, metabolic, or renal syndromes and diseases, including outcomes such as mortality, readmission, rehospitalization, and ED visits, at various time intervals that may or may not follow an index hospitalization event. The systems and methods as described herein may utilize a combination of subject demographic data, clinical data, and other relevant factors to generate risk scores that reflect the likelihood of certain events. By employing machine learning techniques, the systems and methods as described herein may achieve improved accuracy in predicting such events and enable healthcare providers to prioritize resources and interventions based on subjects' risk profiles.

Figure 8:
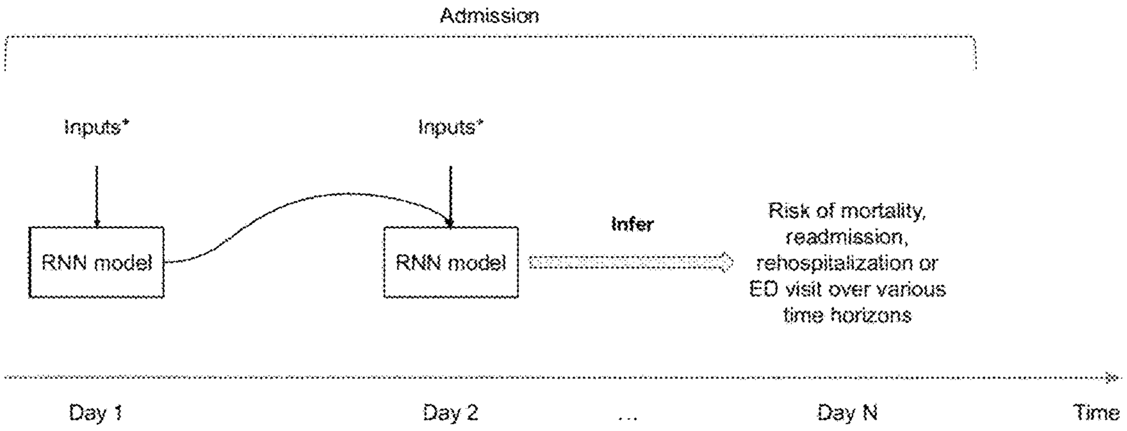
FIG. 8 illustrates another example of a RNN model designed to take in a variety of inputs to generate a probability of mortality or other events within a certain time frame.

FIG. 8 illustrates an example of RNN model designed to take in a variety of inputs to generate a probability of mortality or other events within a certain time frame. The inputs that are fed to the AI/ML model (e.g., RNN model) include, but are not limited to, subject demographics, medical history, and clinical data. Clinical data includes Electronic Health Record (EHR) data (e.g., clinical notes, demographics, lab values, physical examination information, vital signs) and medical images (e.g., chest x-rays, echocardiograms, MRIs, PYP scans, scintigraphy). The AI/ML model uses these inputs to generate a probability of mortality or other events within a certain time frame, including risk of mortality, readmission, rehospitalization, and/or ED visit. The RNN architecture allows the model to analyze temporal data, such as changes in subject vital signs over time. The AI/ML model as described herein has potential applications in the healthcare industry for risk assessment and can aid healthcare providers in making informed decisions about patient care.

Various subject data elements may be collected in the inpatient and/or outpatient environment to be used as input to the AI/ML model, including but not limited to a) demographic information such as age, gender, race, ethnicity, socioeconomic status, and geographic location; b) clinical data such as diagnosis codes, procedure codes, vital signs, laboratory results, medication history, comorbidities, disease severity indicators, and clinical notes; c) historical data such as prior hospitalizations, ED visits, readmissions, and relevant healthcare utilization history. The subject data may be divided into training and test cohorts (e.g., randomly assign 80% of the data to a training cohort and 20% to a testing cohort). The AI/ML model may be built to calculate risk scores for mortality, readmission, rehospitalization, and ED visits at different time intervals, including but not limited to 1 day, 2 days, 3 days, 4 days, 5 days, 6 days, 7 days, 10 days, 14 days, 30 days, 60 days, 90 days, 6 months, 1 year, and 2 years from a given point in time. The AI/ML model may generate probabilities (e.g., likelihood of mortality) for each subject based on the subject's characteristics and/or clinical variables.

In some embodiments, each time window may include such information as the descriptive statistics and number of observations for each clinical variable of interest (e.g., lab results, vital signs, and comorbidities). In some embodiments, data collected prior to the reference hospitalization and/or in the early hours (e.g. the first 24, 48, or 72 hours) of the reference hospitalization may be used to predict outcomes at a later time in the reference hospitalization, such as at the point of discharge. In other embodiments, data collected at any time in the outpatient and/or inpatient environment may be used to predict outcomes after a patient is discharged from the hospital or when the patient is otherwise in the outpatient or home environment.

In some embodiments, the last hidden state of the RNN model may be concatenated with a multi-channel neural network classifier to predict probabilities (e.g., the likelihood of the outcome) given a subject's clinical trajectory. The use of the last hidden state of the RNN model and the multi-channel neural network classifier can improve model accuracy and provide a more detailed understanding of a subject's clinical trajectory. The systems and methods as described herein can be applied to subjects with heart failure, hypertension, atrial fibrillation, amyloidosis, or other cardiovascular, metabolic, or renal syndromes or diseases.

In some embodiments, determining an assessment of a cardiovascular, metabolic, or renal syndrome, disease, or disorder in a subject may further comprise analyzing a biomarker in the subject. In some embodiments, the biomarker may comprise a hemoconcentration marker (e.g., hemoglobin, hematocrit, albumin, uric acid), B-type natriuretic peptide (BNP), N-terminal (NT)-pro hormone BNP (NT-proBNP), creatinine, potassium, troponin, or a combination thereof. In some embodiments, analyzing the biomarker in the subject may further comprise assaying a biological sample obtained or derived from the subject. In some embodiments, the biological sample may comprise blood, plasma, serum, urine, saliva, tissue, derivatives thereof, or a combination thereof.

Figure 9:
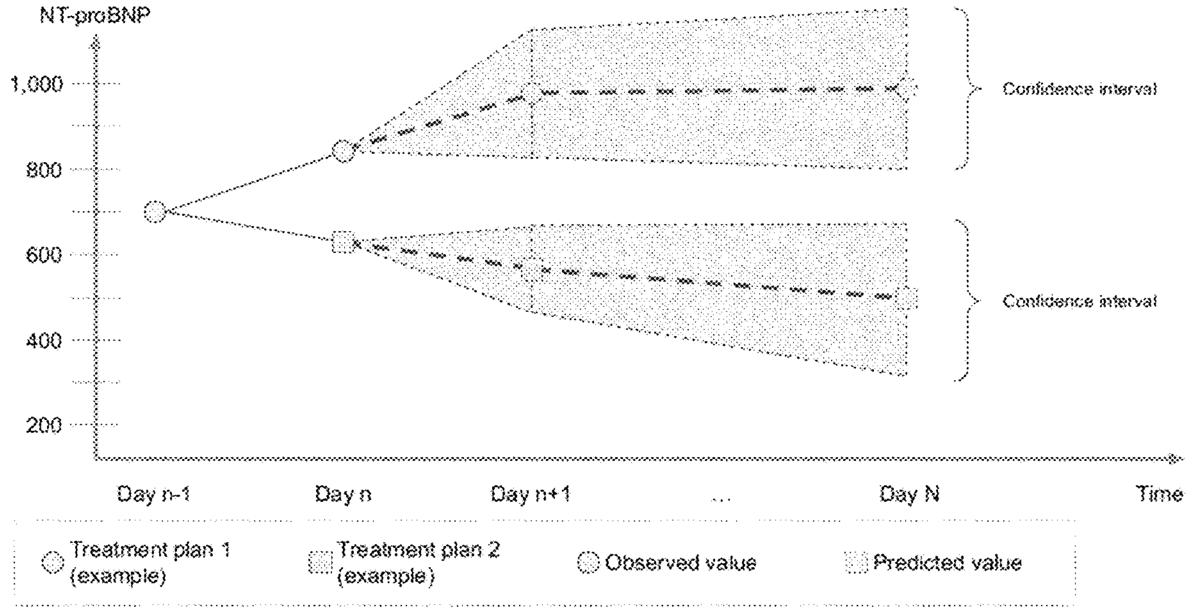
FIG. 9 illustrates an example of prediction of responses of a subject to two different treatment plans over time (e.g., on each of a plurality of days), as measured by NT-proBNP levels.

FIG. 9 illustrates an example of predicted response of a subject to two different treatment plans over time (e.g., on each of a plurality of days), as measured by NT-proBNP levels. Based on the observed NT-proBNP levels on Day n−1 and Day n in patients under treatment plans 1 and 2, respectively, the AI/ML model can predict the trajectory of NT-proBNP levels on Day n+1, n+2, . . . , N.

Figure 10:
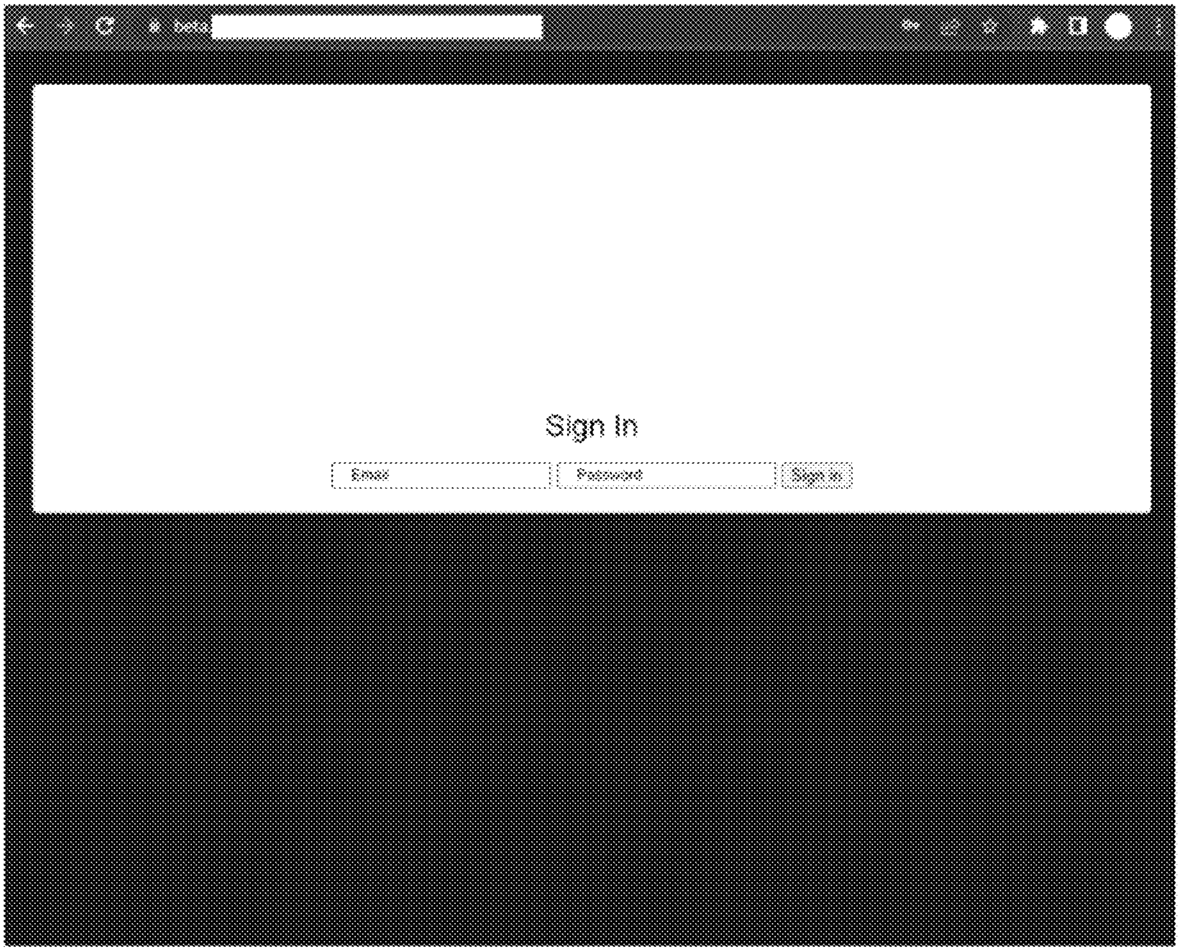
FIG. 10 illustrates a user interface (UI) for users to use the AI/ML models.

FIG. 10 illustrates a user interface (UI) for users to use the AI/ML models. To implement and deploy the models and provide predictions to users, a computer system sends the results from AI/ML models and/or databases to users' computing device interface. Users are prompted to log in before they can query and view results.

Figure 11:
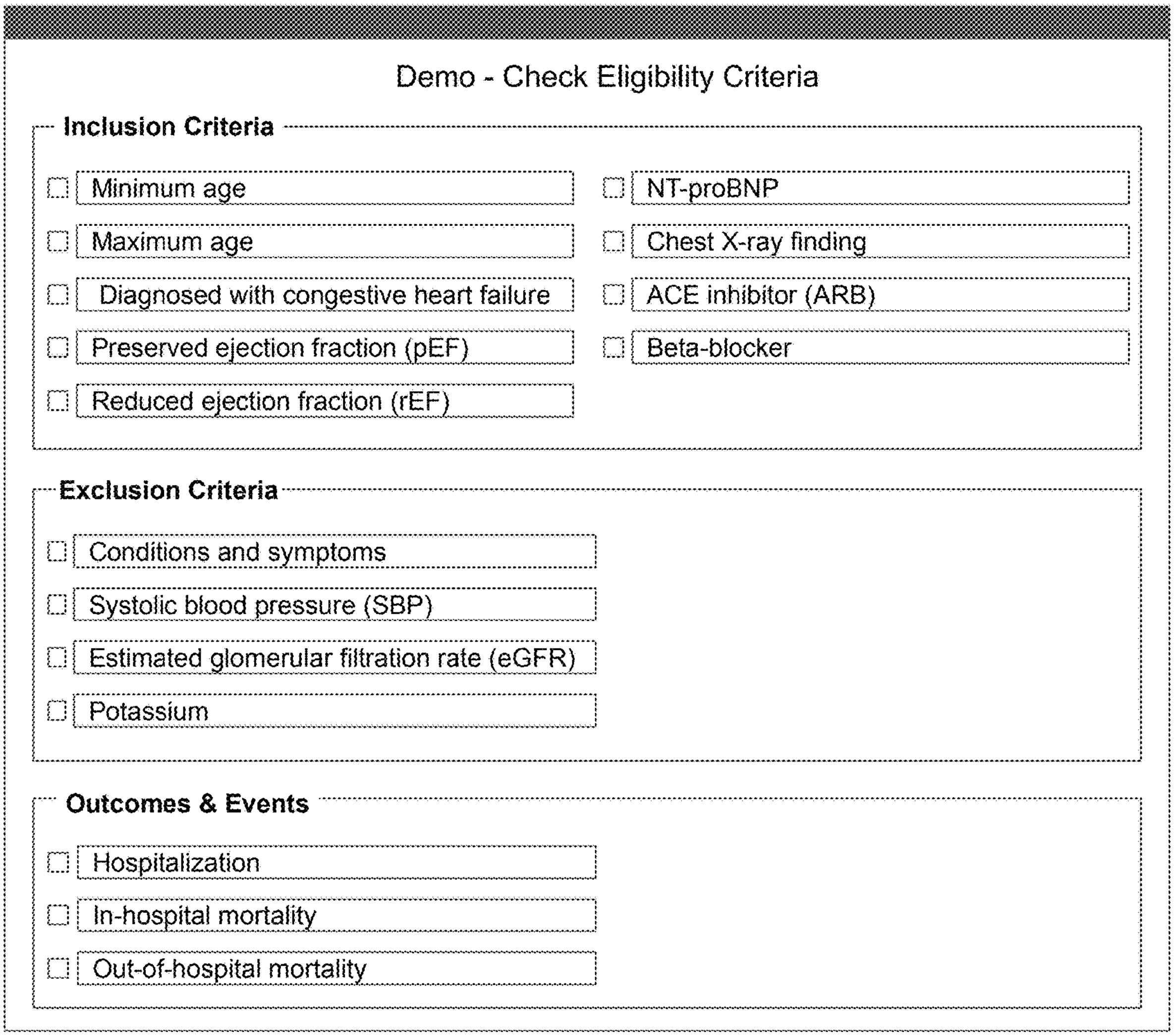
FIG. 11 illustrates a user interface (UI) for users to determine subject eligibility criteria for selecting subjects for clinical trials.

FIG. 11 illustrates a user interface (UI) for users to determine subject eligibility criteria for selecting subjects for clinical trials. The eligibility criteria can include inclusion criteria and exclusion criteria. Once logged in, users can query structured and unstructured data that includes but are not limited to information on demographics (e.g., age), medical images (e.g., echocardiograms, ejection fraction, chest radiographs, pulmonary edema), and clinical data (e.g., lab results such as NT-proBNP and potassium, medication history such as ACE and beta blockers, conditions, symptoms, blood pressure, and estimated glomerular filtration rate). Users can also check the risk of certain adverse events or outcomes of interest, including but not limited to hospitalization and mortality, in certain subsets of subject populations. Users can also iteratively adjust inclusion and exclusion criteria to view outcomes & events for different subject cohorts.

Figure 12:
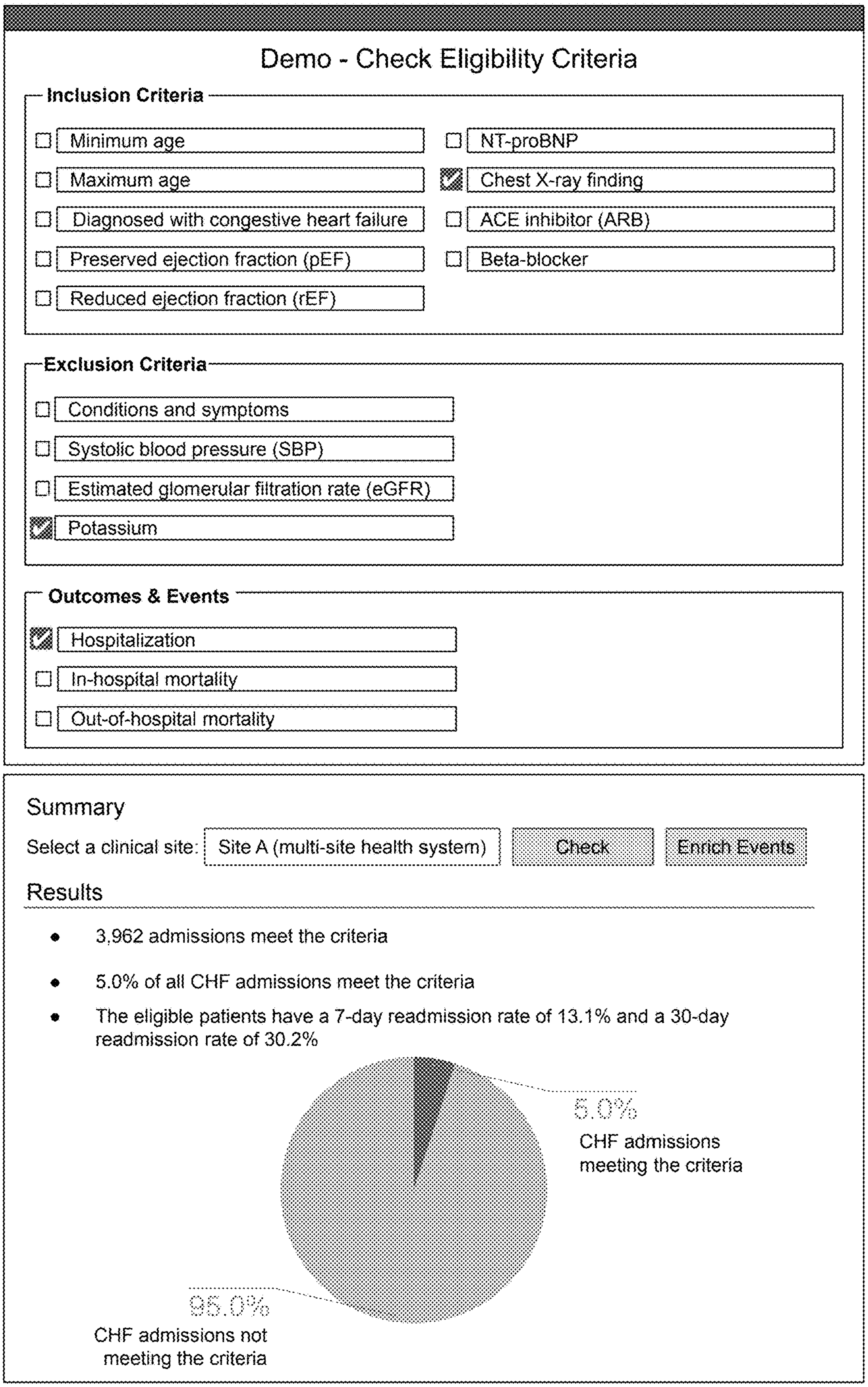
FIG. 12 shows an example of user interface (UI) showing selected subject eligibility criteria, and a summary of eligible subjects under the criteria in the Second Aspect—Example Use Case 3.

FIG. 12 shows an example of user interface (UI) showing selected inclusion criteria and exclusion criteria, and summary of eligible subjects under the criteria in Second Aspect—Example Use Case 3. Users can input certain inclusion criteria that they have in mind, such as age at least 18 but no more than 80; signs of pulmonary edema on chest radiograph. Users can also input exclusion criteria, such as potassium above 5.2 Milliequivalents Per Liter (mEq/L). Users can select an outcome or event of interest, for example, hospitalization, and a clinical site of interest, for example a multi-site health system. As illustrated, users can receive summary statistics for that clinical site. The summary statistics may include but are not limited to, number & percent of admissions that meet the eligibility criteria, seven-day readmission rate, and thirty-day readmission rate.

Figure 13:
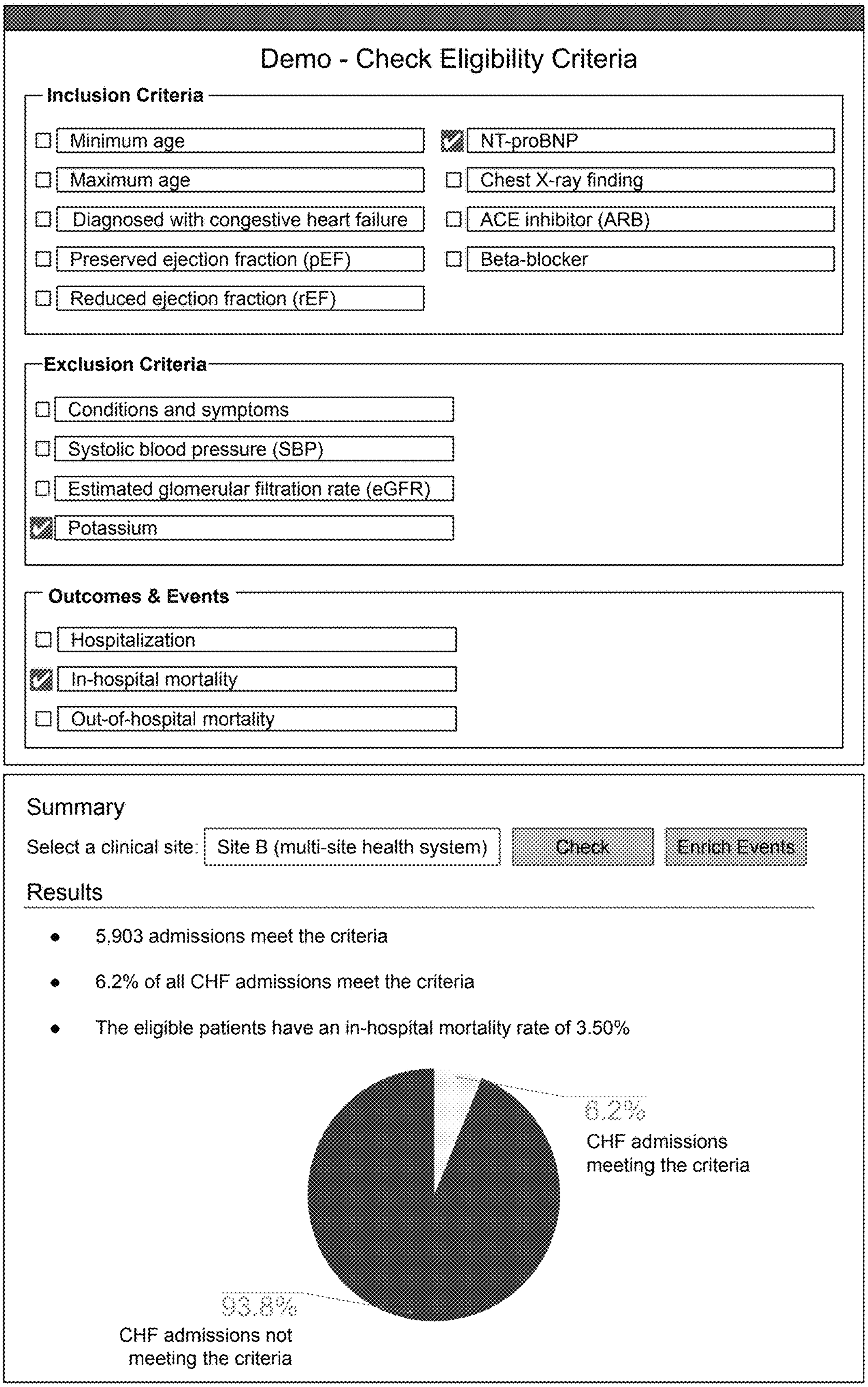
FIG. 13 shows an example of user interface (UI) showing selected subject eligibility criteria, and a summary of eligible subjects under the criteria in the Second Aspect—Example Use Case 3.

FIG. 13 shows an example of user interface (UI) showing selected inclusion criteria and exclusion criteria, and summary of eligible subjects under the criteria in Second Aspect—Example Use Case 3. Users can input certain inclusion criteria that they have in mind, for example, age at least 18 but no more than 80; NT-proBNP above a certain level, for example, above 600 Picograms per milliliter. Users can select an outcome or event of interest, for example, in-hospital mortality. Users can also select a clinical site of interest, for example, a multi-site health system. Users can receive summary statistics for that clinical site. The summary statistics may include but are not limited to, number & percent of admissions that meet the eligibility criteria, and in-hospital mortality rate.

Figure 14:
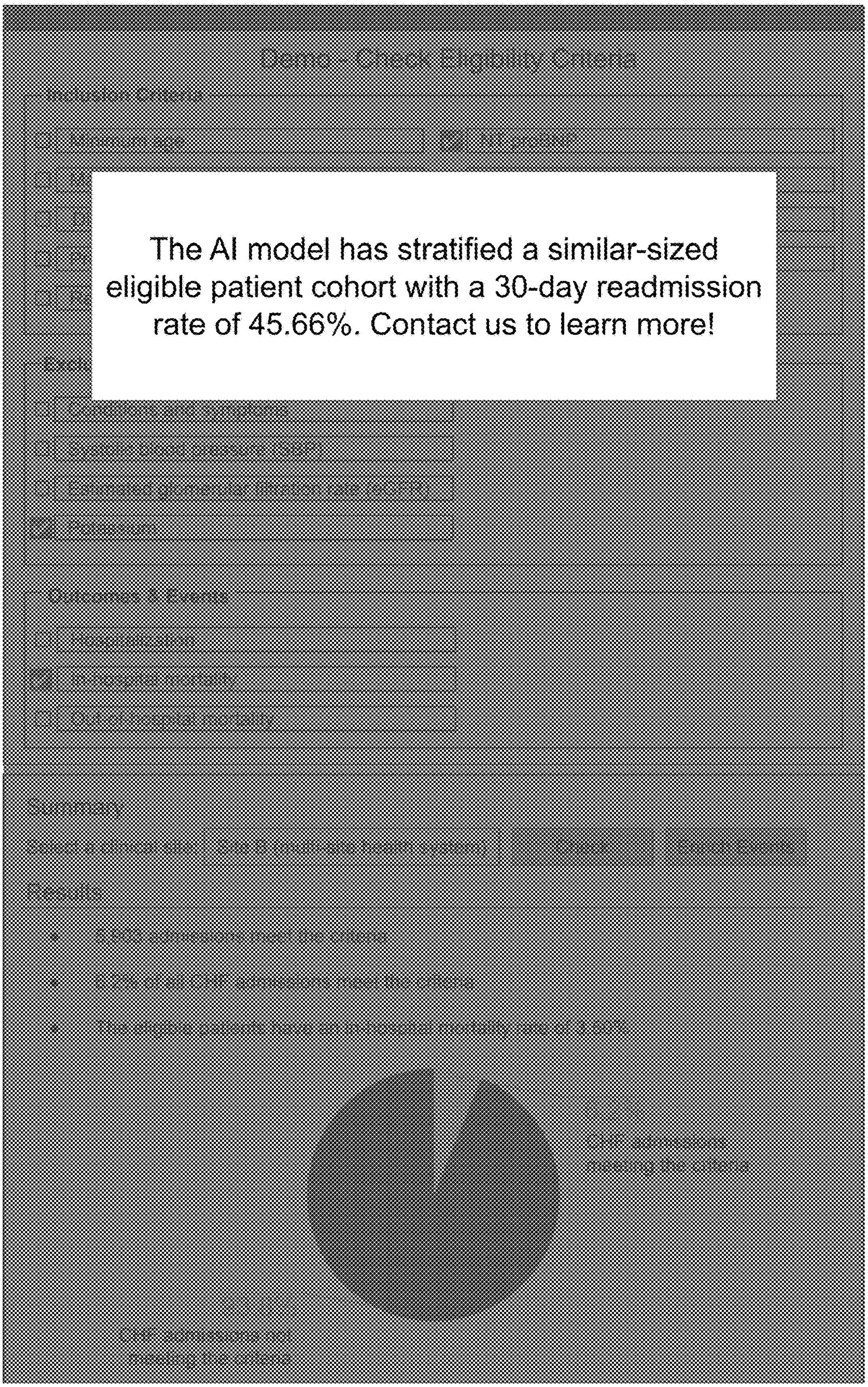
FIG. 14 shows an example of using AI/ML models to optimize eligibility criteria in the Second Aspect—Example Use Case 4.

FIG. 14 shows an example of using AI/ML models to optimize eligibility criteria in Second Aspect—Example Use Case 4. Users can use the AI/ML solutions to optimize eligibility criteria, for example, by finding a cohort of subjects with a higher event rate compared to that of similar-sized cohorts identified by other means.

The present disclosure provides systems and methods for stratifying or phenotyping chronically ill patients, including heart failure patients. The systems and methods may be used in numerous ways to personalize intervention plans, including the following examples use cases.

First Aspect—Example Use Case 1: predicting in-hospital clinical trajectories to enable early interventions shortly after admission.

First Aspect—Example Use Case 2: predicting out-of-hospital risk of adverse events (e.g., hospitalization, readmission, mortality) to inform discharge decisions and post-discharge care.

The present disclosure provides systems and methods for using data query technology and AI/ML solutions to improve the efficiency and efficacy of clinical trials, for example, cardiovascular clinical trials. The example users may comprise clinical trial sponsors (e.g., pharmaceutical companies, medical device manufacturers) and Contract Research Organizations (CROs). Some non-limiting example use cases may comprise i) iteration on inclusion and/or exclusion criteria and visualization of what percent of the patient population in a certain hospital would be eligible and what their event rates would be; and ii) use of AI/ML solutions to optimize eligibility criteria. The example users may also comprise hospitals, health systems, and other healthcare providers. Some non-limiting example use cases may comprise i) joining platform networks to attract clinical trials likely to be successful based on the characteristics of its patient population; and ii) automating the process of reviewing structured & unstructured clinical data to identify and enroll eligible patients.

First Aspect—Example Use Case 1

Anticipating the clinical trajectory of a decompensated HF patient shortly after admission is crucial to plan therapy. BNP and NT-proBNP are commonly measured through lab tests during hospitalization to assess patient status. Predicting the BNP or NT-proBNP trajectory of a patient within the first 48 hours of admission enables early intervention for patients at risk of worsening and improvement in trajectory of response to treatment.

In this use case, three trajectory groups were defined based on how a patient's BNP/NT-proBNP level changes during the hospitalization: 1) worsening or no change, if the discharge BNP was higher than or equal to the admission BNP; 2) inadequate response, if the BNP level was decreased by less than 30%; 3) adequate response, if the BNP level was decreased by more than 30%. Acute HF hospitalization records were collected from a US hospital system. Over 5,000 of these hospitalization records had both admission BNP (collected within 24 hours of admission) and discharge BNP (collected at least 48 hours after admission). The collected data was randomly split into training (80%) and test (20%) sets. The AI/ML model was trained based on the first 48 hours' clinical data to predict which of the three trajectory groups a patient would be in. The model performance was evaluated using the test set. The model achieved an AUC of 0.73 in predicting whether a patient would respond or not. The model performance continued improving over time, for example, as more data was added and the model architecture was improved. This use case demonstrates the potential of leveraging AI/ML models to guide trajectory assessment and interventions.

Users may use the trajectory prediction in various ways. For example, when a patient is determined to have an inadequate response, users may take that information into account to make a number of clinical decisions, including, but not limited to, adjusting the mix and dose of medications (e.g., diuretics) prescribed, recommending other interventions (e.g., a medical device), extending the patient's length of stay in the hospital, or adjusting the discharge pathway.

First and Second Aspects—Example Use Case 2

Multimodal data including images, notes, and structured data measurements were collected during hospitalization and clinical visits. A vast amount of valuable data was being generated but not fully utilized.

The AI/ML models were tested on about 10,000 patient records in a US hospital system, demonstrating an AUC of 0.90 in predicting in-hospital mortality, an AUC of 0.83 in predicting thirty-day mortality, and an AUC of 0.80 in predicting three-month mortality. The model performance continued improving over time. In the context of clinical trials, the AI/ML models achieved the same event rates (thirty-day and three-month mortality rates) with one quarter the size of the patient cohort needed, compared to using elevated BNP or NT proBNP which is currently used in many heart failure (HF) clinical trials.

Users may use out-of-hospital risk prediction in various ways. For example, users may delay discharge of the patient if his/her readmission risk is above a certain threshold. Another example is that users may allocate more resources to the patient post-discharge, including visiting nurses and home monitoring devices.

Second Aspect—Example Use Case 3

Clinical trial sponsors and CROs may access the technology as described herein (e.g., as illustrated in FIG. 10) and use it to check the characteristics of the patient population at a potential trial site (as shown in FIGS. 11-13). If a site has enough of the types of patients the clinical trial sponsors or CROs are looking for, then the sponsor or CRO may decide to partner with that site for the trial. If the site does not have enough of the types of patients the sponsor or CRO is looking for, then the sponsor or CRO may make a number of decisions based on that information, including but not limited to: looking for a different trial site or adjusting the eligibility criteria (e.g., inclusion criteria, exclusion criteria) to achieve certain desired characteristics, including, but not limited to, increased event rates for certain outcomes, improved likelihood of success at a certain site, and greater patient diversity.

Second Aspect—Example Use Case 4

Clinical trial sponsors and CROs may access the technology as described herein (e.g., as illustrated in FIG. 10) and use it to optimize eligibility criteria (e.g., as shown in FIG. 14). The AI/ML technology may be used in various ways to optimize inclusion criteria. For example, rather than using a static BNP cutoff (e.g., BNP>600 pg/mL) as inclusion criteria, users may use AI-optimized criteria that captures subtle indicators in temporal trends and multimodal data. As another example, rather than using CHA2DS2-VASc scores to predict risk of stroke in patients, users may use AI/ML models with better performance. By using AI/ML models to optimize eligibility criteria, clinical trial sponsors and CROs may demonstrate a statistically significant treatment effect on patient populations that are the same size or smaller than the populations that would otherwise be used without AI-optimized eligibility criteria. Hence, the AI/ML models as described herein may enable faster, cheaper, and more efficient clinical trials.

Second Aspect—Example Use Case 5

Hospitals, health systems, and other healthcare providers may join the data query technology platform, where clinical trial sponsors or CROs may view de-identified summary statistics of their patient populations. This can help hospitals, health systems, and other providers market themselves to clinical trial sponsors and attract trials that are likely to be successful based on the characteristics of their patient population.

Second Aspect—Example Use Case 6

Hospitals, health systems, and other providers may access the technology as described herein (e.g., as illustrated in FIG. 10) and use it to check the characteristics of their patient populations. This is useful in a number of ways, including, but not limited to: answering questionnaires from clinical trial sponsors evaluating them as a possible trial site; in the case of multi-site systems, assessing which of their locations best meets a certain trial's eligibility criteria; and in cases where identifiable patient data is available, identifying patients to enroll in particular trials after site selection.

Machine Learning Algorithms

Systems and methods of the present disclosure may utilize or access external capabilities of artificial intelligence techniques to develop signatures for disease states. These signatures may be analyzed to accurately predict a future onset or trajectory of a disease state (e.g., hours to days earlier than with traditional clinical care). Using such a predictive capability, health care providers (e.g., physicians) may be able to make informed, accurate clinical decisions.

The systems and methods of the present disclosure may analyze acquired health data from a subject (patient) to generate a likelihood of the subject having an adverse health condition (e.g., deterioration of the patient's state, occurrence or recurrence of a disease or disorder, or occurrence of a complication). For example, the systems and methods may apply a trained (e.g., prediction) algorithm to the acquired health data to generate the likelihood of the subject having an adverse health condition (e.g., deterioration of the patient's state, occurrence or recurrence of a disease or disorder, or occurrence of a complication). The trained algorithm may comprise an artificial intelligence based classifier, such as a machine learning based classifier, configured to process the acquired health data to generate the likelihood of the subject having the disease or disorder. The machine learning classifier may be trained using clinical datasets from one or more cohorts of patients, e.g., using clinical health data of the patients (e.g., vital sign data) as inputs and known clinical health outcomes (e.g., occurrence or recurrence of a disease or disorder) of the patients as outputs to the machine learning classifier.

The machine learning classifier may comprise one or more machine learning algorithms. Examples of machine learning algorithms may include a support vector machine (SVM), a naïve Bayes classification, a random forest, a neural network (such as a deep neural network (DNN), a recurrent neural network (RNN), a deep RNN, a long short-term memory (LSTM) recurrent neural network (RNN), or a gated recurrent unit (GRU) recurrent neural network (RNN)), deep learning, or other supervised learning algorithm or unsupervised learning algorithm for classification and regression. The machine learning classifier may be trained using one or more training datasets corresponding to patient data.

Training datasets may be generated from, for example, one or more cohorts of patients having common clinical characteristics (features) and clinical outcomes (labels). Training datasets may comprise a set of features and labels corresponding to the features. Features may correspond to algorithm inputs comprising patient demographic information derived from electronic medical records (EMR) and medical observations. Features may comprise clinical characteristics such as, for example, certain ranges or categories of vital sign measurements, such as heart rate, heart rate variability, blood pressure (e.g., systolic and diastolic), respiratory rate, blood oxygen concentration ($SpO_2$), carbon dioxide concentration in respiratory gasses, a hormone level, sweat analysis, blood glucose, body temperature, impedance (e.g., bioimpedance), conductivity, capacitance, resistivity, electromyography, galvanic skin response, neurological signals (e.g., electroencephalography), immunology markers, and other physiological measurements. Features may comprise patient information such as patient age, patient medical history, other medical conditions, current or past medications, and time since the last observation. For example, a set of features collected from a given patient at a given time point may collectively serve as a feature signature, which may be indicative of a health state or status of the patient at the given time point.

For example, ranges of features may be expressed as a plurality of disjoint continuous ranges of continuous measurement values, and categories of features may be expressed as a plurality of disjoint sets of measurement values (e.g., {"high", "low"}, {"high", "normal"}, {"low", "normal"}, {"high", "borderline high", "normal", "low"}, etc.). Clinical characteristics may also include clinical labels indicating the patient's health history, such as a diagnosis of a disease or disorder, a previous administration of a clinical treatment (e.g., a drug, a surgical treatment, chemotherapy, radiotherapy, immunotherapy, etc.), behavioral factors, or other health status (e.g., hypertension or high blood pressure, hyperglycemia or high blood glucose, hypercholesterolemia or high blood cholesterol, history of allergic reaction or other adverse reaction, etc.).

Labels may comprise clinical outcomes such as, for example, a presence, absence, diagnosis, or prognosis of an adverse health condition (e.g., deterioration of the patient's state, occurrence or recurrence of a disease or disorder, or occurrence of a complication) in the patient. Clinical outcomes may include a temporal characteristic associated with the presence, absence, diagnosis, or prognosis of the adverse health condition in the patient. For example, temporal characteristics may be indicative of the patient having had an occurrence of the adverse health condition within a certain period of time after a previous clinical outcome (e.g., being discharged from the hospital, undergoing an organ transplantation or other surgical operation, undergoing a clinical procedure, etc.). Such a period of time may be, for example, about 1 hour, about 2 hours, about 3 hours, about 4 hours, about 6 hours, about 8 hours, about 10 hours, about 12 hours, about 14 hours, about 16 hours, about 18 hours, about 20 hours, about 22 hours, about 24 hours, about 2 days, about 3 days, about 4 days, about 5 days, about 6 days, about 7 days, about 10 days, about 2 weeks, about 3 weeks, about 4 weeks, about 1 month, about 2 months, about 3 months, about 4 months, about 6 months, about 8 months, about 10 months, about 1 year, or more than about 1 year.

Input features may be structured by aggregating the data into bins or alternatively using a one-hot encoding with the time since the last observation included. Inputs may also include feature values or vectors derived from the previously mentioned inputs, such as cross-correlations calculated between separate vital sign measurements over a fixed period of time, and the discrete derivative or the finite difference between successive measurements. Such a period of time may be, for example, about 1 hour, about 2 hours, about 3 hours, about 4 hours, about 6 hours, about 8 hours, about 10 hours, about 12 hours, about 14 hours, about 16 hours, about 18 hours, about 20 hours, about 22 hours, about 24 hours, about 2 days, about 3 days, about 4 days, about 5 days, about 6 days, about 7 days, about 10 days, about 2 weeks, about 3 weeks, about 4 weeks, about 1 month, about 2 months, about 3 months, about 4 months, about 6 months, about 8 months, about 10 months, about 1 year, or more than about 1 year.

Training records may be constructed from sequences of observations. Such sequences may comprise a fixed length for ease of data processing. For example, sequences may be zero-padded or selected as independent subsets of a single patient's records.

The machine learning classifier algorithm may process the input features to generate output values comprising one or more classifications, one or more predictions, or a combination thereof. For example, such classifications or predictions may include a binary classification of a disease or a non-disease state, a classification between a group of categorical labels (e.g., 'no disease, 'disease apparent', and 'disease likely'), a likelihood (e.g., relative likelihood or probability) of developing a particular disease or disorder, a score indicative of a 'presence of urgent symptoms', a 'risk factor' for the likelihood of adverse health events (e.g., hospitalization or mortality) of the patient, a prediction of the time at which the patient is expected to have developed the disease or disorder or experienced an adverse health event, and a confidence interval for any numeric predictions. Various machine learning techniques may be cascaded such that the output of a machine learning technique may also be used as input features to subsequent layers or subsections of the machine learning classifier.

In order to train the machine learning classifier model (e.g., by determining weights and correlations of the model) to generate real-time classifications or predictions, the model can be trained using datasets. Such datasets may be sufficiently large to generate statistically significant classifications or predictions.

Examples of databases include open source databases, and may comprise de-identified patient records, vital sign measurements, laboratory test results, procedures, and medications prescribed. The database may contain data collected from multiple different hospitals, rather than a single hospital.

In some cases, datasets are annotated or labeled. Datasets may be split into subsets (e.g., discrete or overlapping), such as a training dataset, a development dataset, and a test dataset. For example, a dataset may be split into a training dataset comprising 80% of the dataset, a development dataset comprising 10% of the dataset, and a test dataset comprising 10% of the dataset. The training dataset may comprise about 10%, about 20%, about 30%, about 40%, about 50%, about 60%, about 70%, about 80%, or about 90% of the dataset. The development dataset may comprise about 10%, about 20%, about 30%, about 40%, about 50%, about 60%, about 70%, about 80%, or about 90% of the dataset. The test dataset may comprise about 10%, about 20%, about 30%, about 40%, about 50%, about 60%, about 70%, about 80%, or about 90% of the dataset. Training sets (e.g., training datasets) may be selected by random sampling of a set of data corresponding to one or more patient cohorts to ensure independence of sampling. Alternatively, training sets (e.g., training datasets) may be selected by proportionate sampling of a set of data corresponding to one or more patient cohorts to ensure independence of sampling.

To improve the accuracy of model predictions and reduce overfitting of the model, the datasets may be augmented to increase the number of samples within the training set. For example, data augmentation may comprise rearranging the order of observations in a training record. To accommodate datasets having missing observations, methods to impute missing data may be used, such as forward-filling, back-filling, linear interpolation, and multi-task Gaussian processes. Datasets may be filtered to remove confounding factors.

The machine learning classifier may comprise one or more neural networks, such as a deep neural network (DNN), a recurrent neural network (RNN), or a deep RNN. The recurrent neural network may comprise units which can be long short-term memory (LSTM) units or gated recurrent units (GRU). For example, the machine learning classifier may comprise an algorithm architecture comprising a long short-term memory (LSTM) recurrent neural network (RNN), with a set of input features such as vital sign measurements, patient medical history, and patient demographics. Neural network techniques, such as dropout or regularization, may be used during training the machine learning classifier to prevent overfitting.

When the machine learning classifier generates a classification or a prediction of a disease, disorder, or complication, an alert or alarm may be generated and transmitted to a health care provider, such as a physician, nurse, or other member of the patient's treating team within a hospital. Alerts may be transmitted via an automated phone call, a short message service (SMS) or multimedia message service (MMS) message, an e-mail, or an alert within a dashboard. The alert may comprise output information such as a prediction of a disease, disorder, or complication, a likelihood of the predicted disease, disorder, or complication, a time until an expected onset of the disease, disorder, or condition, a confidence interval of the likelihood or time, or a recommended course of treatment for the disease, disorder, or complication.

An LSTM recurrent neural network may comprise a plurality of sub-networks, each of which is configured to generate a classification or prediction of a different type of output information (e.g., a disease classification and a time until the onset of disease or adverse health event).

To validate the performance of the machine learning classifier model, different performance metrics may be generated. For example, an area under the receiver-operating curve (AUROC) may be used to determine the diagnostic capability of the machine learning classifier. For example, the machine learning classifier may use classification thresholds which are adjustable, such that specificity and sensitivity are tunable, and the receiver-operating curve (ROC) can be used to identify the different operating points corresponding to different values of specificity and sensitivity.

In some cases, such as when datasets are not sufficiently large, cross-validation may be performed to assess the robustness of a machine learning classifier model across different training and testing datasets.

In some cases, while a machine learning classifier model may be trained using a dataset of records which are a subset of a single patient's observations, the performance of the classifier model's discrimination ability (e.g., as assessed using an AUROC) is calculated using the entire record for a patient. To calculate performance metrics such as sensitivity, specificity, accuracy, positive predictive value (PPV), negative predictive value (NPV), AUPRC, AUROC, or similar, the following definitions may be used. A "false positive" may refer to an outcome in which if an alert or alarm has been incorrectly or prematurely activated (e.g., before the actual onset of, or without any onset of, a disease state or condition) fires too early. A "true positive" may refer to an outcome in which an alert or alarm has been activated at the correct time (within a predetermined buffer or tolerance), and the patient's record indicates the disease or condition. A "false negative" may refer to an outcome in which no alert or alarm has been activated, but the patient's record indicates the disease or condition. A "true negative" may refer to an outcome in which no alert or alarm has been activated, and the patient's record does not indicate the disease or condition.

The machine learning classifier may be trained until certain predetermined conditions for accuracy or performance are satisfied, such as having minimum desired values corresponding to diagnostic accuracy measures. For example, the diagnostic accuracy measure may correspond to prediction of a likelihood of occurrence of an adverse health condition such as deterioration or a disease or disorder in the subject. As another example, the diagnostic accuracy measure may correspond to prediction of a likelihood of deterioration or recurrence of an adverse health condition such as a disease or disorder for which the subject has previously been treated. For example, a diagnostic accuracy measure may correspond to prediction of likelihood of recurrence of a disease or disorder in a subject who has previously been treated for the disease or disorder. Examples of diagnostic accuracy measures may include sensitivity, specificity, positive predictive value (PPV), negative predictive value (NPV), accuracy, area under the precision-recall curve (AUPRC), and area under the curve (AUC) of a Receiver Operating Characteristic (ROC) curve (AUROC) corresponding to the diagnostic accuracy of detecting or predicting an adverse health condition.

For example, such a predetermined condition may be that the sensitivity of predicting occurrence or recurrence of the adverse health condition such as deterioration or a disease or disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the specificity of predicting occurrence or recurrence of the adverse health condition such as deterioration or a disease or disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting occurrence or recurrence of the adverse health condition such as deterioration or a disease or disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting occurrence or recurrence of the adverse health condition such as deterioration or a disease or disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve (AUROC) of predicting occurrence or recurrence of the adverse health condition such as deterioration or a disease or disorder comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

As another example, such a predetermined condition may be that the area under the precision-recall curve (AUPRC) of predicting occurrence or recurrence of the adverse health condition such as deterioration or a disease or disorder comprises a value of at least about 0.10, at least about 0.15, at least about 0.20, at least about 0.25, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained classifier may be trained or configured to predict occurrence or recurrence of the adverse health condition such as deterioration or a disease or disorder with a sensitivity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained classifier may be trained or configured to predict occurrence or recurrence of the adverse health condition such as deterioration or a disease or disorder with a specificity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained classifier may be trained or configured to predict occurrence or recurrence of the adverse health condition such as deterioration or a disease or disorder with a positive predictive value (PPV) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained classifier may be trained or configured to predict occurrence or recurrence of the adverse health condition such as deterioration or a disease or disorder with a negative predictive value (NPV) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

In some embodiments, the trained classifier may be trained or configured to predict occurrence or recurrence of the adverse health condition such as deterioration or a disease or disorder with an area under the curve (AUC) of a Receiver Operating Characteristic (ROC) curve (AUROC) of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained classifier may be trained or configured to predict occurrence or recurrence of the adverse health condition such as deterioration or a disease or disorder with an area under the precision-recall curve (AUPRC) of at least about 0.10, at least about 0.15, at least about 0.20, at least about 0.25, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some embodiments, the trained classifier may be trained or configured to predict occurrence or recurrence of the adverse health condition such as deterioration or a disease or disorder over a period of time before the actual occurrence or recurrence of the adverse health condition (e.g., a period of time including a window beginning about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, about 36 hours, about 48 hours, about 72 hours, about 96 hours, about 120 hours, about 6 days, or about 7 days prior to the onset of the health condition, and ending at the onset of the health condition).

Computer Systems

Figure 24:
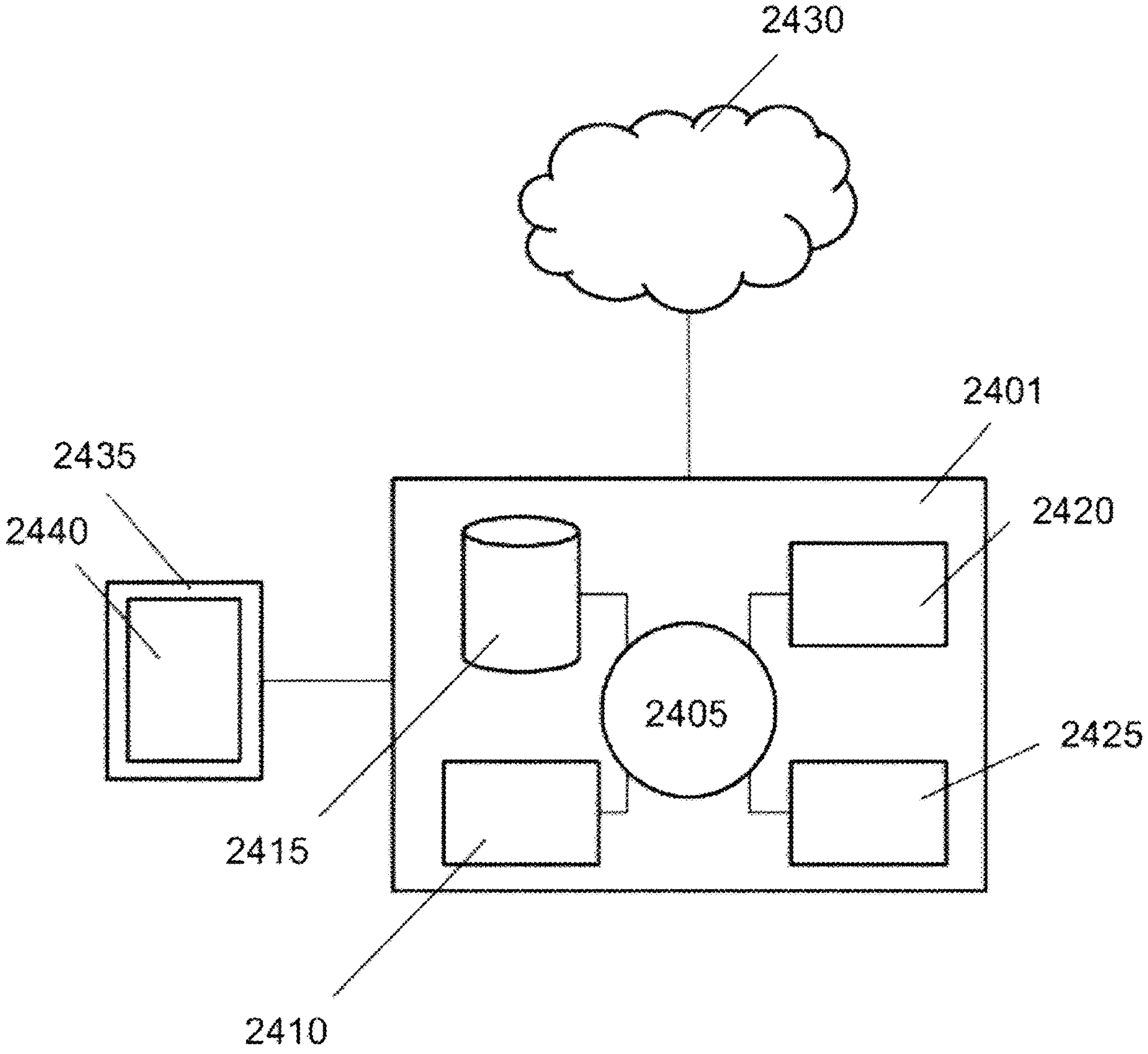
FIG. 24 illustrates a computer system that is programmed or otherwise configured to implement methods provided herein.

The present disclosure provides computer systems that are programmed to implement methods of the disclosure. FIG. 24 shows a computer system 2401 that is programmed or otherwise configured to, for example, (i) train and test a trained algorithm, (ii) use the trained algorithm to process data to determine a treatment response of a subject, (iii) determine a quantitative measure indicative of a treatment response of a subject, (iv) identify or monitor a cardiovascular, metabolic, and/or renal syndrome, disease, or disorder of the subject, and (v) electronically output a report indicative of the cardiovascular, metabolic, and/or renal syndrome, disease, or disorder of the subject.

The computer system 2401 can regulate various aspects of analysis, calculation, and generation of the present disclosure, such as, for example, (i) training and testing a trained algorithm, (ii) using the trained algorithm to process data to determine a treatment response of a subject, (iii) determining a quantitative measure indicative of a treatment response of a subject, (iv) identifying or monitoring a cardiovascular, metabolic, or renal syndrome, disease, or disorder of the subject, and (v) electronically outputting a report indicative of the cardiovascular, metabolic, or renal syndrome, disease, or disorder of the subject. The computer system 2401 can be an electronic device of a user or a computer system that is remotely located with respect to the electronic device. The electronic device can be a mobile electronic device.

The computer system 2401 includes a central processing unit (CPU, also "processor" and "computer processor" herein) 2405, which can be a single core or multi core processor, or a plurality of processors for parallel processing. The computer system 2401 also includes memory or memory location 2410 (e.g., random-access memory, read-only memory, flash memory), electronic storage unit 2415 (e.g., hard disk), communication interface 2420 (e.g., network adapter) for communicating with one or more other systems, and peripheral devices 2425, such as cache, other memory, data storage and/or electronic display adapters. The memory 2410, storage unit 2415, interface 2420 and peripheral devices 2425 are in communication with the CPU 2405 through a communication bus (solid lines), such as a motherboard. The storage unit 2415 can be a data storage unit (or data repository) for storing data. The computer system 2401 can be operatively coupled to a computer network ("network") 2430 with the aid of the communication interface 2420. The network 2430 can be the Internet, an internet and/or extranet, or an intranet and/or extranet that is in communication with the Internet.

The network 2430 in some cases is a telecommunication and/or data network. The network 2430 can include one or more computer servers, which can enable distributed computing, such as cloud computing. For example, one or more computer servers may enable cloud computing over the network 2430 ("the cloud") to perform various aspects of analysis, calculation, and generation of the present disclosure, such as, for example, (i) training and testing a trained algorithm, (ii) using the trained algorithm to process data to determine a treatment response of a subject, (iii) determining a quantitative measure indicative of a treatment response of a subject, (iv) identifying or monitoring a cardiovascular, metabolic, or renal syndrome, disease, or disorder of the subject, and (v) electronically outputting a report indicative of the cardiovascular, metabolic, or renal syndrome, disease, or disorder of the subject. Such cloud computing may be provided by cloud computing platforms such as, for example, Amazon Web Services (AWS), Microsoft Azure, Google Cloud Platform, and IBM cloud. The network 2430, in some cases with the aid of the computer system 2401, can implement a peer-to-peer network, which may enable devices coupled to the computer system 2401 to behave as a client or a server.

The CPU 2405 may comprise one or more computer processors and/or one or more graphics processing units (GPUs). The CPU 2405 can execute a sequence of machine-readable instructions, which can be embodied in a program or software. The instructions may be stored in a memory location, such as the memory 2410. The instructions can be directed to the CPU 2405, which can subsequently program or otherwise configure the CPU 2405 to implement methods of the present disclosure. Examples of operations performed by the CPU 2405 can include fetch, decode, execute, and writeback.

The CPU 2405 can be part of a circuit, such as an integrated circuit. One or more other components of the system 2401 can be included in the circuit. In some cases, the circuit is an application specific integrated circuit (ASIC).

The storage unit 2415 can store files, such as drivers, libraries and saved programs. The storage unit 2415 can store user data, e.g., user preferences and user programs. The computer system 2401 in some cases can include one or more additional data storage units that are external to the computer system 2401, such as located on a remote server that is in communication with the computer system 2401 through an intranet or the Internet.

The computer system 2401 can communicate with one or more remote computer systems through the network 2430. For instance, the computer system 2401 can communicate with a remote computer system of a user. Examples of remote computer systems include personal computers (e.g., portable PC), slate or tablet PC's (e.g., Apple® iPad, Samsung® Galaxy Tab), telephones, smart phones (e.g., Apple® iPhone, Android-enabled device, Blackberry®), or personal digital assistants. The user can access the computer system 2401 via the network 2430.

Methods as described herein can be implemented by way of machine (e.g., computer processor) executable code stored on an electronic storage location of the computer system 2401, such as, for example, on the memory 2410 or electronic storage unit 2415. The machine executable or machine readable code can be provided in the form of software. During use, the code can be executed by the processor 2405. In some cases, the code can be retrieved from the storage unit 2415 and stored on the memory 2410 for ready access by the processor 2405. In some situations, the electronic storage unit 2415 can be precluded, and machine-executable instructions are stored on memory 2410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as the main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, a cloud-based storage, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2401 can include or be in communication with an electronic display 2435 that comprises a user interface (UI) 2440 for providing, for example, (i) a visual display indicative of training and testing of a trained algorithm, (ii) a visual display of data indicative of a treatment response of a subject, (iii) a quantitative measure of a treatment response of a subject, (iv) an identification of a subject as having a cardiovascular, metabolic, or renal syndrome, disease, or disorder, or (v) an electronic report indicative of the cardiovascular, metabolic, or renal syndrome, disease, or disorder of the subject. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 2405. The algorithm can, for example, (i) train and test a trained algorithm, (ii) use the trained algorithm to process data to determine a treatment response of a subject, (iii) determine a quantitative measure indicative of a treatment response of a subject, (iv) identify or monitor a cardiovascular, metabolic, or renal syndrome, disease, or disorder of the subject, and (v) electronically output a report indicative of the cardiovascular, metabolic, or renal syndrome, disease, or disorder of the subject.

EXAMPLES

Example 1: Amyloidosis

Using systems and methods of the present disclosure, various approaches for measuring response to amyloidosis treatment may include, but are not limited to, measuring:

- All-cause mortality over 12 months;
- Cardiovascular-related hospitalizations over 12 months;
- Change in 6-minute walk test (6MWT) at Month 12;
- Change in albumin, BNP or NT-proBNP, and/or troponin I at Month 12;
- Change in left ventricular mass (LVM) from cardiac MRI at Month 12;
- Change in strain from echo at Month 12;
- Kansas City Cardiomyopathy Questionnaire (KCCQ) at Month 12; and
- Change in PYP scintigraphy.

When predicting response to amyloidosis medications, example use cases may include, but are not limited to:

- Anticipate response to TTR silencers such as Patisiran or Inotersen;
- Anticipate response to TTR stabilizers such as Tafamidis or Diflunisal;
- Identify potential responders, super responders, and/or non-responders;
- Support clinical decision-making when a doctor or other clinician is prescribing amyloidosis treatment in the hospital;
- Support clinical decision-making when a doctor or other clinician is prescribing amyloidosis treatment in an outpatient clinic;
- Support clinical decision-making when a doctor or other clinician is prescribing amyloidosis treatment during a home visit or via telehealth;
- Support prior-authorization process for doctors, other clinicians, or other members of patient care teams at hospitals or other provider organizations;
- Support prior-authorization process for medical insurers; and
- Help clinical trial sponsors (e.g., pharmaceutical companies, medical device manufacturers) optimize eligibility criteria, site selection, and/or patient enrollment when designing and/or conducting clinical trials.

Help contract research organizations (CROs) optimize eligibility criteria, site selection, and/or patient enrollment when designing and/or conducting clinical trials.

Example 2: Diuretics

Using systems and methods of the present disclosure, various approaches for measuring response to diuretics may include, but are not limited to, measuring:

- Change in BNP or NT-proBNP;
- Change in body weight;
- Change in creatinine;
- Change in hemoconcentration markers (e.g., hemoglobin, hematocrit, albumin, uric acid); and
- Change in potassium.

When predicting response to diuretics, example use cases may include, but are not limited to:

- Anticipate response to Loop diuretics such as Furosemide, Bumetanide, and Torsemide;
- Anticipate response to Thiazide diuretics such as Chlorothiazide, Hydrochlorothiazide, and Metolazone;
- Identify potential responders, super responders, and/or non-responders;
- Make predictions to help optimize the diuretic regimen, for example, predict the optimal type and/or mix of diuretics for a particular patient, and predict the optimal dose for each diuretic;
- Support clinical decision-making when a doctor or other clinician is prescribing diuretics in the hospital;
- Support clinical decision-making when a doctor or other clinician is prescribing diuretics in an outpatient clinic;
- Support clinical decision-making when a doctor or other clinician is prescribing diuretics during a home visit or via telehealth;
- Help clinical trial sponsors (e.g., pharmaceutical companies, medical device manufacturers) optimize eligibility criteria, site selection, and/or patient enrollment when designing and/or conducting clinical trials; and
- Help contract research organizations (CROs) optimize eligibility criteria, site selection, and/or patient enrollment when designing and/or conducting clinical trials.

Example 3: GDMT

Using systems and methods of the present disclosure, various approaches for measuring response to guideline-directed medical therapy (GDMT) may include, but are not limited to, measuring:

- Change in blood pressure;
- Change in ejection fraction (EF);
- Change in glomerular filtration rate (GFR) or estimated glomerular filtration rate (eGFR);
- Change in heart rate; and
- Change in potassium.

When predicting response to guideline directed medical therapy (GDMT), example use cases may include, but are not limited to:

- Anticipate response to Beta blockers (e.g., Carvedilol, Metoprolol Succinate XL);
- Anticipate response to Mineralocorticoid receptor antagonists (MRAs) (e.g., Spironolactone; Eplerenone);
- Anticipate response to Renin-angiotensin-aldosterone system inhibitors (RAASis) (e.g., Angiotensin-converting enzyme inhibitors (ACEis), Angiotensin receptor blockers (ARBs), angiotensin receptor neprilysin inhibitors (ARNis));
- Anticipate response to Sodium glucose co-transporter 2 inhibitors (SGLT2is);
- Identify potential responders, super responders, and/or non-responders;
- Make predictions to help optimize the GDMT regimen, for example, predict the optimal dose with which to initialize a particular treatment, and predict the optimal cadence with which to titrate a particular treatment;
- Support clinical decision-making when a doctor or other clinician is prescribing GDMT in the hospital;
- Support clinical decision-making when a doctor or other clinician is prescribing GDMT in an outpatient clinic;
- Support clinical decision-making when a doctor or other clinician is prescribing GDMT during a home visit or via telehealth;
- Help clinical trial sponsors (e.g., pharmaceutical companies, medical device manufacturers) optimize eligibility criteria, site selection, and/or patient enrollment when designing and/or conducting clinical trials; and
- Help contract research organizations (CROs) optimize eligibility criteria, site selection, and/or patient enrollment when designing and/or conducting clinical trials.

Example 4: Predicting In-Hospital Clinical Trajectories Using Machine Learning in Patients Admitted with Acute Decompensated Heart Failure Using methods and systems of the present disclosure, in-hospital clinical trajectories were predicted using machine learning in patients admitted with acute decompensated heart failure (e.g., as described by, for example, Ruizhi Liao et al., "PREDICTING IN-HOSPITAL CLINICAL TRAJECTORIES USING MACHINE LEARNING IN PATIENTS ADMITTED WITH ACUTE DECOMPENSATED HEART FAILURE", J Am Coll Cardiol, Mar. 5, 2023, Vol. 81, No. 8_Supplement, which is incorporated by reference herein in its entirety).

Heart failure (HF) is a leading cause of hospitalization in the United States, accounting for nearly 1 million hospitalizations every year and contributing to more than half of annual US healthcare spending for HF. Despite this high expenditure, in-hospital mortality remains consistently high, between 4% to 12%, with a 20% to 30% risk of death within one year of discharge.

In-hospital clinical trajectories of patients admitted with decompensated HF are important determinants of post hospital management and prognosis. Continued reassessment of in-hospital clinical trajectories is not only recommended, but recognizing patterns earlier in the hospital course may be crucial to plan in-hospital therapy and interventions and to help patients improve towards target. Retrospective analysis of data from hospitalizations for acute decompensated heart failure (ADHF) may suggest novel phenotypes that could enable clinicians to anticipate how a patient might respond to treatment, and thereby adjust interventions. Patients hospitalized with acute decompensated heart failure (ADHF) have different clinical trajectories during hospitalization, which impacts length of stay and risk of readmission. Early recognition of in-hospital trajectories may be important, especially for those patients not responding to treatment.

Artificial intelligence (AI) has the potential to exploit large amounts of high-dimensional and heterogenous retrospective data to identify underlying patterns and discover phenotypes. Modern machine learning algorithms that operate by leveraging neural network models are particularly good at capturing complex and non-linear relationships between data variables from big data and are therefore ideal to aid in risk stratification of clinical trajectories.

The target for in-hospital management of ADHF is often decongestion. Hemoconcentration can be used as a surrogate for decongestion during diuresis. In this example, the in-hospital trajectory of decompensated HF patients using hemoglobin was characterized into two trajectory groups: hemoconcentration, indicating improving towards target, and no hemoconcentration, indicating stalled or worsening. The outcomes in the two trajectory groups were indicated. The AL/ML algorithms were established to predict the likelihood of hemoconcentration as a surrogate for improving towards target using clinically available data in the first 48 hours of admission and evaluated the utility of AI/ML models to phenotype patients as hemoconcentration vs no hemoconcentration.

The target for in-hospital management of ADHF is often decongestion. Hemoconcentration can be used as a surrogate for decongestion during diuresis. In this example, the in-hospital trajectory of decompensated HF patients using hemoglobin was characterized into two trajectory groups: hemoconcentration, indicating improving towards target, and no hemoconcentration, indicating stalled or worsening. The outcomes in the two trajectory groups were indicated. The AL/ML algorithms were established to predict the likelihood of hemoconcentration as a surrogate for improving towards target using clinically available data in the first 48 hours of admission and evaluated the utility of AI/ML models to phenotype patients as hemoconcentration vs no hemoconcentration.

Study Population and Data

Figure 15:
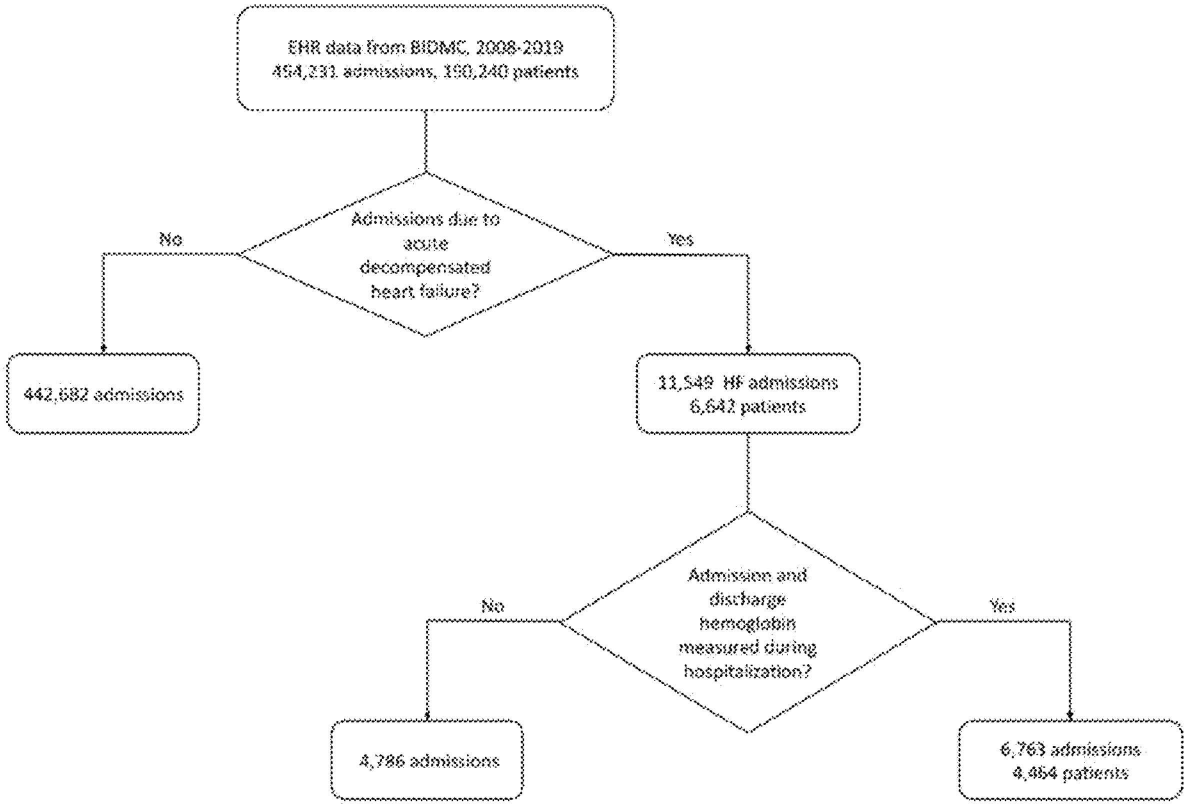
FIG. 15 illustrates a workflow of subject cohort selection.

This example included patients admitted at a multi-site health system, whose primary International Classification of Diseases (ICD) diagnosis code is HF. We extracted about 200,000 patients' hospitalization records and about 11,000 HF hospitalization records from the multi-site health system. FIG. 15 illustrates a workflow of patient cohort selection. Retrospective data was de-identified and obtained from the healthcare systems' Electronic Health Records (EHRs), including demographics, laboratory values, vital signs, body weight, medication administration data, diagnosis ICD codes, from inpatient admission encounters.

Clinical Trajectory Characterization and Label Generation

Hemoconcentration, defined by an increase in hemoglobin level, was used as a proxy to assess decongestion. The first laboratory value collected within the first 48 hours of admission was defined as admission lab. The last lab collected after the 4th day (96 hours) of admission before discharge was considered as discharge lab. A patient with an increase in hemoglobin at discharge relative to the admission hemoglobin was labeled as hemoconcentration; Otherwise they were labeled as no hemoconcentration. The baseline characteristics of the HF admissions that have both admission and discharge hemoglobin measures available are shown in Table 1. The outcomes were compared, including out-of-hospital mortality, readmission due to heart failure, and all-cause readmission between the hemoconcentration and no hemoconcentration group.

TABLE 1

Patient baseline characteristics of hospitalizations for acute decompensated heart failure that had both admission hemoglobin and discharge hemoglobin available.

| | Overall | Hemoconcentration | No hemoconcentration | P-Value |
|---|---|---|---|---|
| n | 6,763 | 3,423 (50.6%) | 3,340 (49.4%) | |
| Demographics | | | | |
| Age, yrs, mean (SD) | 73.3 (14.1) | 72.9 (14.4) | 73.7 (13.7) | 0.02 |
| Gender, male, n (%) | 3594 (53.1) | 1824 (53.3) | 1770 (53.0) | 0.83 |
| Measurements | | | | |
| Systolic BP, mmHg, mean (SD) | 133.3 (27.3) | 134.4 (27.2) | 132.0 (27.4) | 0.00 |
| Diastolic BP, mmHg, mean (SD) | 74.9 (104.1) | 73.4 (18.0) | 76.5 (148.2) | 0.34 |
| Heart rate, beats/min, mean (SD) | 85.4 (22.9) | 84.8 (19.6) | 85.9 (26.0) | 0.10 |

TABLE 1-continued

| Patient baseline characteristics of hospitalizations for acute decompensated heart failure that had both admission hemoglobin and discharge hemoglobin available. | | | | |
|---|---|---|---|---|
| | Overall | Hemoconcentration | No hemoconcentration | P-Value |
| Weight, kg, mean (SD) | 86.7 (31.4) | 87.9 (33.6) | 85.7 (29.5) | 0.20 |
| Laboratory | | | | |
| Albumin, g/dl, mean (SD) | 3.5 (0.5) | 3.5 (0.5) | 3.5 (0.5) | 0.17 |
| BUN, mmol/l, mean (SD) | 39.1 (25.5) | 38.7 (25.9) | 39.5 (25.2) | 0.22 |
| Creatinine, mg/dl, mean (SD) | 1.9 (1.6) | 1.9 (1.7) | 1.9 (1.4) | 0.78 |
| eGFR, ml/min, mean (SD) | 46.2 (25.4) | 47.6 (26.6) | 44.7 (24.0) | <0.01 |
| Hematocrit, %, mean (SD) | 33.4 (6.3) | 32.2 (6.3) | 34.7 (5.9) | <0.01 |
| Hemoglobin, g/dl, mean (SD) | 10.6 (2.1) | 10.2 (2.1) | 11.1 (2.0) | <0.01 |
| Charlson comorbidity | | | | |
| Any malignancy, n (%) | 481 (7.1) | 226 (6.6) | 255 (7.6) | 0.11 |
| Cerebrovascular disease, n (%) | 403 (6.0) | 185 (5.4) | 218 (6.5) | 0.06 |
| Chronic pulmonary disease, n (%) | 2824 (41.8) | 1437 (42.0) | 1387 (41.5) | 0.72 |
| Dementia, n (%) | 276 (4.1) | 128 (3.7) | 148 (4.4) | 0.17 |
| Diabetes with chronic complication, n (%) | 1788 (26.4) | 928 (27.1) | 860 (25.7) | 0.21 |
| Diabetes without chronic complication, n (%) | 1626 (24.0) | 835 (24.4) | 791 (23.7) | 0.51 |
| Hemiplegia or paraplegia, n (%) | 31 (0.5) | 10 (0.3) | 21 (0.6) | 0.06 |
| HIV, n (%) | 37 (0.5) | 18 (0.5) | 19 (0.6) | 0.94 |
| Metastatic solid tumor, n (%) | 131 (1.9) | 68 (2.0) | 63 (1.9) | 0.83 |
| Mild liver disease, n (%) | 464 (6.9) | 247 (7.2) | 217 (6.5) | 0.26 |
| Moderate or severe liver disease, n (%) | 100 (1.5) | 51 (1.5) | 49 (1.5) | 1.00 |
| Myocardial infarction, n (%) | 1520 (22.5) | 743 (21.7) | 777 (23.3) | 0.13 |
| Peptic ulcer disease, n (%) | 74 (1.1) | 44 (1.3) | 30 (0.9) | 0.16 |
| Peripheral vascular disease, n (%) | 1025 (15.2) | 511 (14.9) | 514 (15.4) | 0.62 |
| Renal disease, n (%) | 3834 (56.7) | 1903 (55.6) | 1931 (57.8) | 0.07 |
| Rheumatic disease, n (%) | 295 (4.4) | 159 (4.6) | 136 (4.1) | 0.27 |

Model Development and Evaluation

Figure 16:
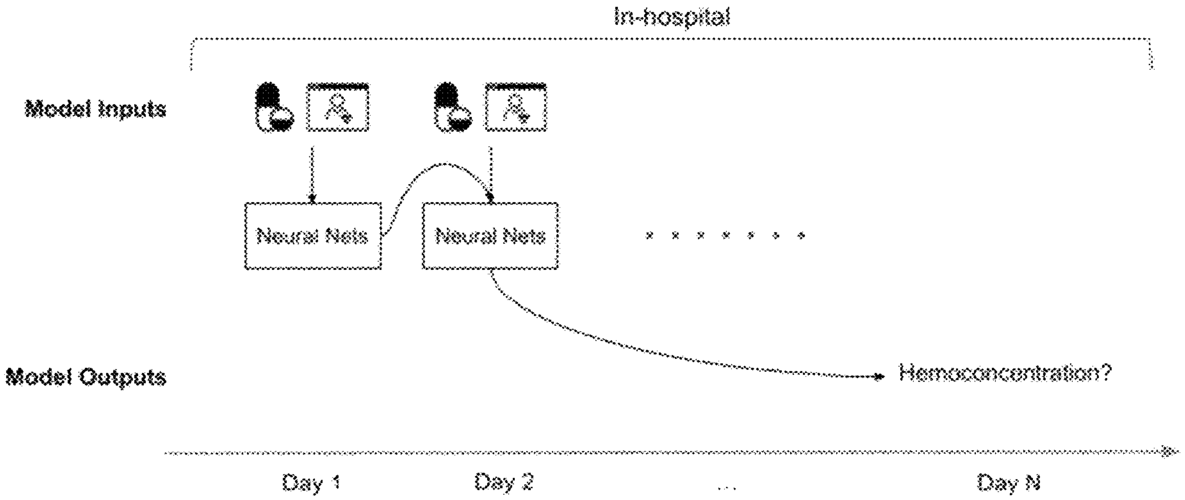
FIG. 16 illustrates an example of a RNN model that predicts hemoconcentration based on clinical data available in the first 48 hours of admission.

A recurrent neural network (RNN) model was built to learn features from clinical data variables and diuretic regimen available in the first 48 hours of admission to predict whether or not this patient will have hemoconcentration at discharge. FIG. 16 illustrates a RNN model that predicts hemoconcentration based on clinical data available in the first 48 hours of admission. Table 2 summarizes the clinical data variables and diuretic drugs as input for the AI/ML model.

TABLE 2

Examples of clinical data variables and diuretic drugs from the first 48 hours of admission that may be used as inputs for the AI/ML model.

| Data category | Data variable |
|---|---|
| Body weight | Body weight |
| Charlson Comorbidities | Any malignancy |
| | Cerebrovascular disease |
| | Chronic pulmonary disease |
| | Dementia |
| | Diabetes with chronic complication |

TABLE 2-continued

Examples of clinical data variables and diuretic drugs from the first 48 hours of admission that may be used as inputs for the AI/ML model.

| Data category | Data variable |
|---|---|
| | Diabetes without chronic complication |
| | Hemiplegia or paraplegia |
| | HIV |
| | Metastatic solid tumor |
| | Mild liver disease |
| | Moderate or severe liver disease |
| | Myocardial infarction |
| | Peptic ulcer disease |
| | Peripheral vascular disease |
| | Renal disease |
| | Rheumatic disease |
| Demographics | Age |
| | Gender |
| Glomerular filtration rate (GFR) | Estimated GFR (eGFR) |
| Laboratory tests | Albumin |
| | BUN |
| | Creatinine |
| | Hematocrit |
| | Hemoglobin |
| | NTproBNP |
| | Potassium |
| | Sodium |
| | Uric Acid |
| Vital signs | Diastolic blood pressure (arterial) |
| | Diastolic blood pressure (pulmonary artery) |
| | Heart rate |
| | Oxygen saturation |
| | Respiratory rate |
| | Systolic blood pressure (arterial) |
| | Systolic blood pressure (pulmonary artery) |
| | Temperature |
| Loop diuretics | Bumetanide (intravenous) |
| | Bumetanide (oral and/or nasal) |
| | Furosemide (intravenous) |
| | Furosemide (oral and/or nasal) |
| | Torsemide (oral and/or nasal) |

TABLE 2-continued

Examples of clinical data variables and diuretic drugs from the first 48 hours of admission that may be used as inputs for the AI/ML model.

| Data category | Data variable |
|---|---|
| Thiazide diuretics | Chlorothiazide (intravenous) |
| | Hydrochlorothiazide (oral and/or nasal) |
| | Metolazone (oral) |
| Potassium-sparing diuretic | Spironolactone (oral and/or nasal) |

The utility of the AI/ML model to phenotype patients as hemoconcentration vs no hemoconcentration was evaluated. The HF admission records with both admission and discharge hemoglobin levels available were randomly split into training (50% of the patients, n=2,204) and test (~50% of the patients, n=2,260) sets. There was no patient overlap between the training set and the test set. The RNN model was pre-trained on the data from patients that were not in the test set. The RNN model was then fine-tuned on the training set and evaluated the machine learning model performance on the test set in predicting whether a patient will have hemoconcentration at discharge. The outcomes of the two patient groups (hemoconcentration vs. no hemoconcentration) phenotyped by the AI/ML model were also compared.

Patient Characteristics and Outcomes

Outcomes of the 6,763 admission encounters that have both admission hemoglobin and discharge hemoglobin measures are presented in Table 3. Overall, 3,340 (49.4%) encounters had no increase in hemoglobin from admission to discharge (no hemoconcentration), and 3,423 (50.6%) had an increase (hemoconcentration). The mortality rates of the admission encounters with hemoconcentration at discharge are significantly lower compared to hospitalizations without hemoconcentration, consistent with prior studies.

TABLE 3

Patient outcomes of hospitalizations that had hemoconcentration vs. no hemoconcentration.

| | Overall | Hemoconcentration | No hemoconcentration | P-Value |
|---|---|---|---|---|
| n | 6,763 | 3,423 (50.6%) | 3,340 (49.4%) | |
| Mortality | | | | |
| 30-day mortality, n (%) | 405 (6.0) | 165 (4.8) | 240 (7.2) | <0.01 |
| 6-month mortality, n (%) | 1,445 (21.4) | 630 (18.4) | 815 (24.4) | <0.01 |
| 1-year mortality, n (%) | 2,114 (31.3) | 944 (27.6) | 1,170 (35.0) | <0.01 |
| Readmission | | | | |
| 30-day readmission due to HF, n (%) | 765 (11.3) | 372 (10.9) | 393 (11.8) | 0.26 |
| 6-month readmission due to HF, n (%) | 1,869 (27.6) | 938 (27.4) | 931 (27.9) | 0.69 |
| 1-year readmission due to HF, n (%) | 2,282 (33.7) | 1,171 (34.2) | 1,111 (33.3) | 0.43 |

Figure 17:
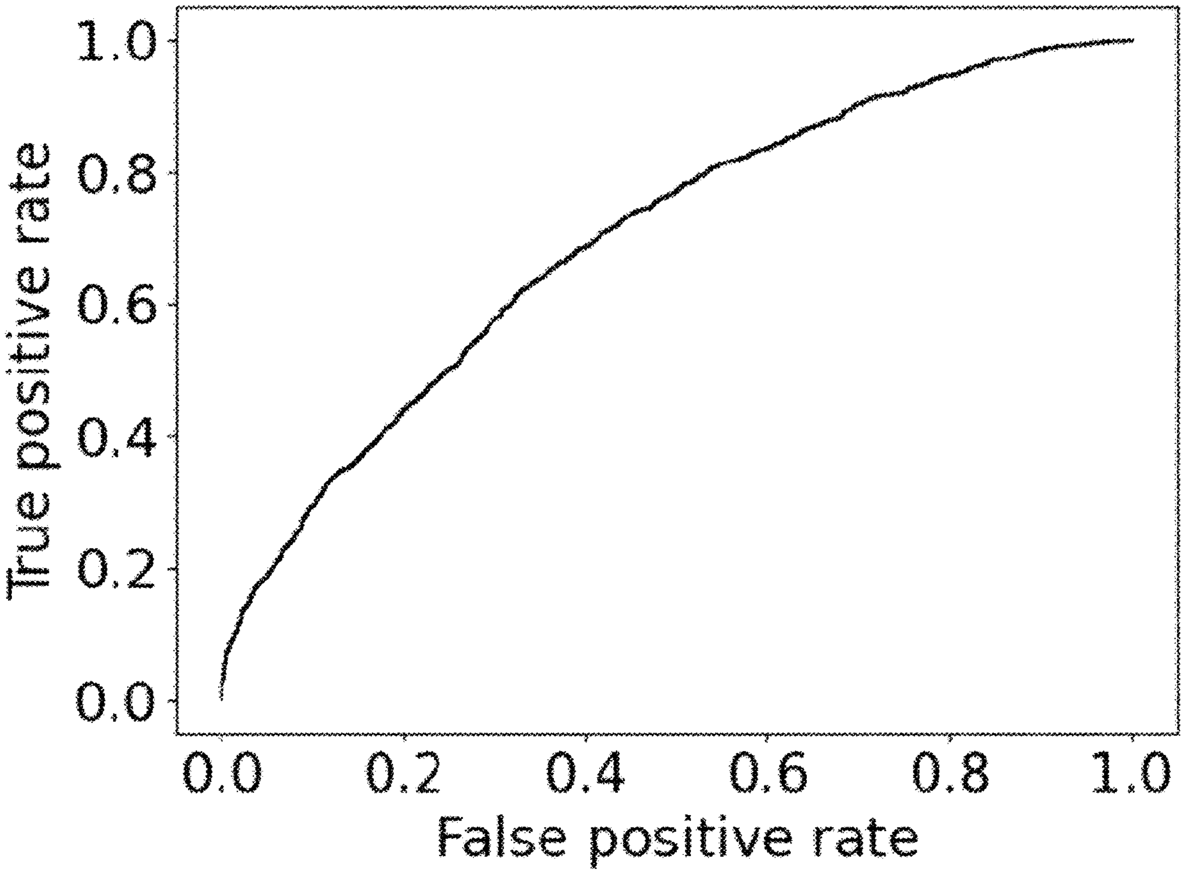
FIG. 17 shows a sensitivity-specificity curve in predicting hemoconcentration.

Predicting Hemoconcentration 74,326 patients and their associated 131,426 admission encounters were used to pre-train and fine tune the RNN model for hemoconcentration prediction in the first 48 hours of hospital stay. The model was evaluated on the holdout test set, including 2,260 patients and their 3,418 hospitalizations. The model achieved an Area Under the Curve (AUC) of 0.70 (95% CI: 0.68-0.72). FIG. 17 shows a sensitivity-specificity curve in predicting hemoconcentration. As illustrated, a positive sample is considered as an admission encounter that had hemoconcentration.

A threshold for the probabilistic AI/ML model was selected such that the sum of sensitivity and specificity was maximized and applied the threshold for predicting hemoconcentration based on the clinical data available in the first 48 hours of admission. In the test set, based on the predicted hemoconcentration status, the patient outcomes were compared and summarized in Table 4.

TABLE 4

Patient outcomes of hospitalizations that were predicted to have hemoconcentration vs. no hemoconcentration based on the clinical data available in the first 48 hours of admission.

| | Overall | Predicted to have hemoconcentration | Predicted to have no hemoconcentration | P-Value |
|---|---|---|---|---|
| n | 3,418 | 1,717 (50.2%) | 1,701 (49.8%) | |
| Mortality | | | | |
| 30-day mortality, n (%) | 206 (6.0) | 95 (5.5) | 111 (6.5) | 0.25 |
| 6-month mortality, n (%) | 745 (21.8) | 343 (20.0) | 402 (23.6) | 0.01 |
| 1-year mortality, n (%) | 1,084 (31.7) | 493 (28.7) | 591 (34.7) | <0.01 |
| Readmission | | | | |
| 30-day readmission due to HF, n (%) | 397 (11.6) | 198 (11.5) | 199 (11.7) | 0.92 |
| 6-month readmission due to HF, n (%) | 935 (27.4) | 458 (26.7) | 477 (28.0) | 0.39 |
| 1-year readmission due to HF, n (%) | 1,150 (33.6) | 574 (33.4) | 576 (33.9) | 0.82 |

In this example, an AI/ML model was developed that can help clinicians anticipate a HF patient's clinical trajectory early in the hospitalization and thereby adjust their treatment plans. Current consensus among clinical experts is that the pathway to improve the outcomes of patients hospitalized for ADHF begins with admission, specifically to start assessing a patient's clinical trajectory continuously during admission. The assessment can translate into different management strategies throughout the hospital stay and post-discharge and therefore may affect both in-hospital and post-hospital outcomes.

Three main in-hospital trajectories are defined as improving towards target, stalled, and not improved/worsening. Prior studies have demonstrated that hemoconcentration during the hospital stay, especially when occurring late in the hospitalization, is associated with improved outcomes. Therefore, hemoconcentration can be used as a surrogate for decongestion and improving towards target. No hemoconcentration can be a sign or stalled or not improved/worsening. This example chose an increase in hemoglobin as an indication of hemoconcentration. Other measures such as albumin, hematocrit may also be included to define hemoconcentration.

It is crucial during the early stage of hospitalization to identify whether or not an ADHF patient will improve towards target, so that the clinical team can adjust their management strategies as needed, for example, if the patient is not expected to improve towards target. Various models may be used for risk stratification early in the hospitalization. For instance, B-type natriuretic peptide (BNP) level has been used as a primary predictor of mortality. Studies that involve multivariate models have been focusing on predicting mortality or rehospitalization. Distinct from prior studies, this example leveraged an RNN model with transfer learning to predict in-hospital trajectories based on clinical information collected in the first 48 hours of admission. The RNN model was architected to capture subtle indicators in temporal trends. The transfer learning algorithm held promise to learn from a broader data domain and overcome the challenges of limited training samples. The AI/ML model as described herein may enable the analysis of big data, as well as the determination of or phenotyping those patients who may improve. The anticipation of clinical trajectories can imply post-discharge patient outcomes (e.g., as shown in Table 4) and thereby translate into strategies to address risk factors and to minimize risk going forward.

The AI/ML model as described herein can phenotype patients as hemoconcentration vs. no hemoconcentration as a surrogate for clinical trajectories. Doing so in the early hours of hospitalization can offer healthcare providers an opportunity to adjust their treatment plans as needed. Expert consensus recommends ongoing assessment during the course of clinical care of patients. The AI/ML model as described herein can be readily modified. For example, the prediction of clinical trajectories can be made every 24 hours after the first 48 hours, using, e.g., new clinical data coming in each day.

Example 5: Use of Synthetic Data and Machine Learning to Predict Mortality in Hospitalized Patients with Heart Failure (HF)

Heart failure (HF) remains a leading cause of morbidity and mortality in the United States, accounting for about one million admissions annually. This immense burden on patients and health systems has led to significant interest in developing new risk prediction models that identify patients at high risk of clinical decompensation. AI/ML models have superior discriminatory ability over traditional methods for predicting outcomes in HF patients. However, the availability of large, multi-dimensional datasets for model training and testing remains a significant barrier, and access to such highly granular data is often limited by patient privacy and data security concerns.

Synthetic patient data may be a privacy-preserving alternative to human-subject data for AI/ML model training. This example describes training a multi-dimensional, non-linear AI/ML model that predicts mortality in hospitalized HF patients using synthetic patient data. The feasibility of using synthetic patient data was evaluated by comparing the model's performance with models trained on actual patient data.

The synthetic dataset was then randomly divided into training (80%) and validation (20%) cohorts that were used to train a RNN model to generate mortality probabilities for each synthetic HF patient. Each time window included the descriptive statistics and number of observations for each clinical variable of interest (e.g., lab results, vital signs, and comorbidities). The last hidden state of the RNN model was concatenated with a multi-channel neural network classifier to predict the likelihood of the outcome given a patient's clinical trajectory. The same process was performed with the original (de-identified) patient data. Area under the receiver operating characteristic curves (AUC) for mortality prediction was calculated for both the synthetic and original data sets and used to evaluate and compare model performance.

Figure 18:
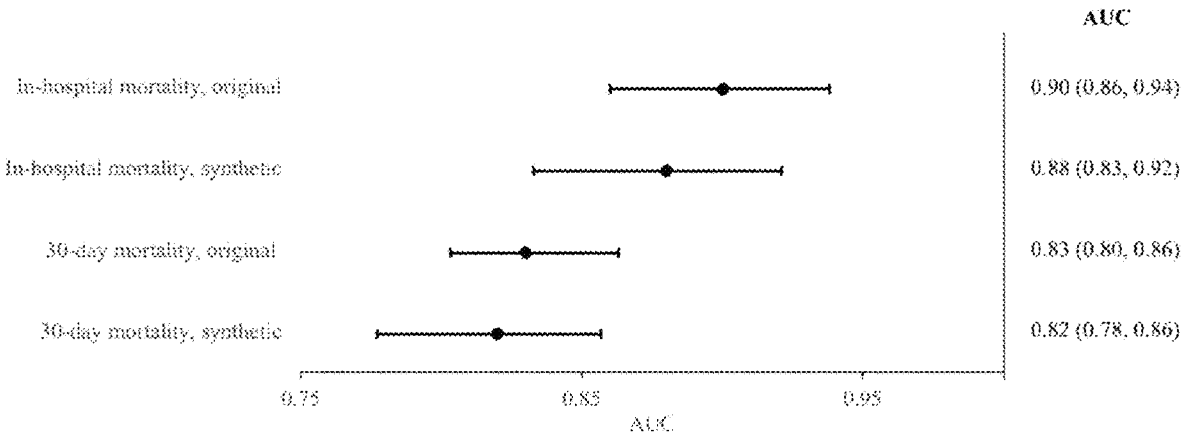
FIG. 18 shows a forest plot of mean AUC for mortality prediction by the training cohort.

A cohort of about 70,000 HF real-world patients admitted between May 1999 and February 2022 was identified, from which a synthetic cohort was generated. FIG. 18 shows a forest plot of mean AUC for mortality prediction by the training cohort. As illustrated, the mean AUC for in-hospital and thirty-day mortality was above 0.8 and broadly similar between the original and synthetic data sets. The results demonstrated the usefulness of the RNN model in predicting patient mortality and the feasibility of synthetic data to replace human-subject data for this task.

Example 6: Use of Machine Learning for Risk Stratification for Congestive Heart Failure (CHF) Patients In this example, the AI/ML model was used for risk stratification for CHF patients. The data for hyper-parameter tuning comprised about 25,000 CHF patients from a multi-site health system in New England and about 280,000 CHF patients from a U.S. multi-site integrated health system. The data for training and testing the AI/ML model comprised about 280,000 CHF patients from the U.S. multi-site integrated health system. Table 5 lists the risk stratification results for the CHF patients predicted by the AI/ML model. The trained AI/ML model showed satisfactory performance (e.g., overall accuracy, sensitivity, specificity, precision) in risk stratification for CHF patients.

TABLE 5

Risk stratification results for the CHF patients predicted by the AI/ML model.

| | All-cause mortality | Mortality for cardio-vascular causes | Hospital readmission for all causes | Hospital readmission for cardiovascular causes |
|---|---|---|---|---|
| Area under the Receiver Operating Characteristic (AUROC) | 0.85 | 0.86 | 0.69 | 0.60 |
| Area under the Precision Recall Curve (AUPRC) | 0.94 | 0.22 | 0.88 | 0.61 |
| Overall accuracy | 0.77 | 0.79 | 0.64 | 0.58 |
| Sensitivity | 0.77 | 0.79 | 0.64 | 0.58 |
| Specificity | 0.77 | 0.79 | 0.64 | 0.58 |
| Precision | 0.89 | 0.16 | 0.87 | 0.60 |
| Negative predictive value | 0.56 | 0.99 | 0.32 | 0.55 |
| Positive likelihood ratio | 3.28 | 3.75 | 1.78 | 1.35 |
| Negative likelihood ratio | 0.30 | 0.27 | 0.56 | 0.74 |
| F1 score | 0.833 | 0.27 | 0.74 | 0.59 |

Figure 19:
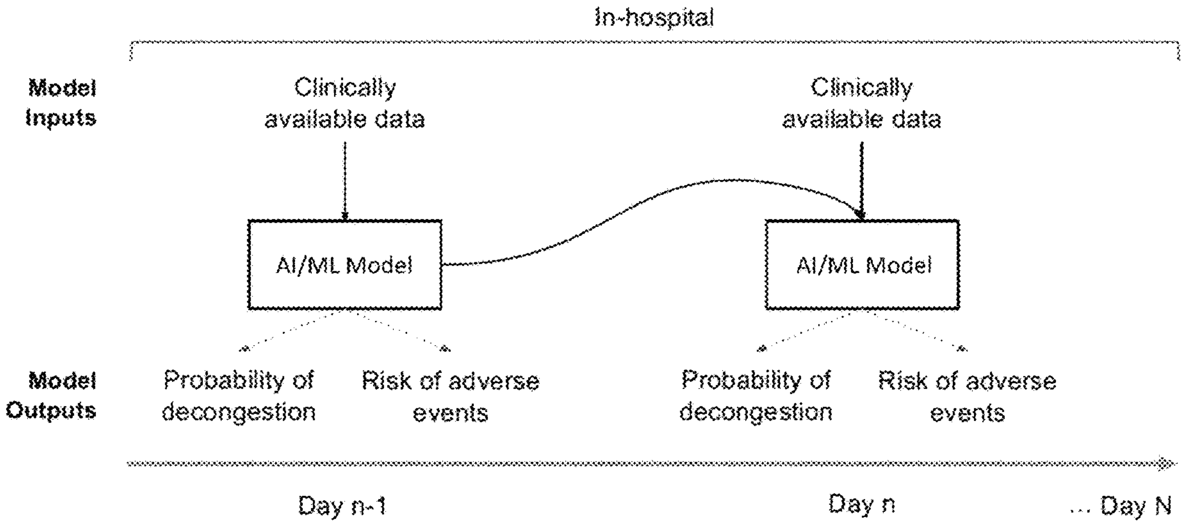
FIG. 19 illustrates an example of AI/ML models designed to take clinically available data as input and generate a probability of decongestion and a risk of adverse events within a certain time frame.

Example 7: Use of Machine Learning for Optimizing In-Hospital Diuretic Regimen of Patients In this example, the AI/ML model is trained to optimize the in-hospital diuretic regiment and to predict in-hospital decongestion for HF patients. FIG. 19 illustrates an example of AI/ML models designed to take clinically available data as input and generate a probability of decongestion and a risk of adverse events within a certain time frame. Clinically available data may comprise body weight, comorbidities, demographics, glomerular filtration rate, laboratory tests, vital signs, and diuretic treatment of patients. Adverse events may comprise kidney injury and hypokalemia.

Figure 20:
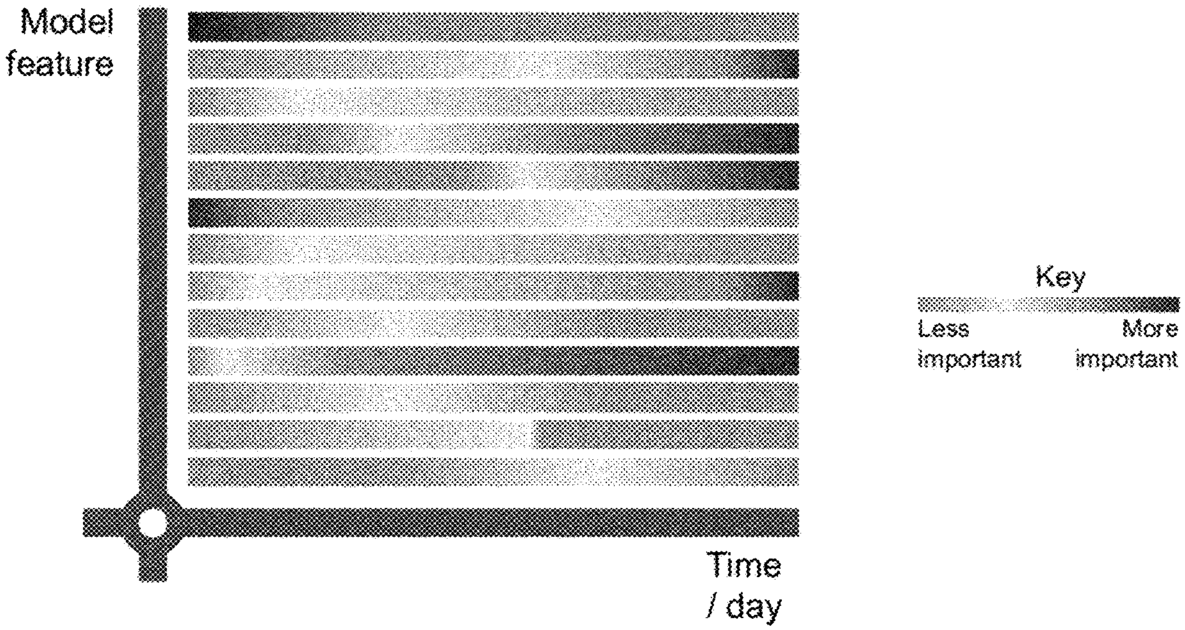
FIG. 20 illustrates an example of saliency map indicative feature importance in the prediction.

FIG. 20 illustrates a saliency map indicative of feature importance in the prediction. As illustrated, the x-axis shows temporal variables (e.g., time/day), and the y-axis shows a list of model features used in the prediction. The saliency map may be individualized for the patient based on the patient's clinical health data. The saliency map may be generated for each time point among a plurality of distinct time points. Each of the set of feature importance values may be visualized in a row on the saliency map. Each of the set of feature importance values may be represented in different colors on the saliency map. As illustrated in FIG. 20, for example, the darker the shading is, the more important the feature. The saliency map may indicate one or more actionable clinical variables from among the set of clinical health data.

Example 8: Use of Machine Learning for Risk Stratification of Cardiac Amyloidosis Patients This example focused on developing and enhancing the AI/ML model for cardiac amyloidosis. Cardiac amyloidosis can lead to heart failure. Many studies have shown that currently, cardiac amyloidosis has been under-diagnosed. There are emerging treatments that can potentially slow down or reverse the progression of this disease. This example leveraged patient data from a multi-site health system that spans the U.S. Midwest, Southwest, and Southeast to enhance the AI/ML model to risk stratify cardiac amyloidosis patients at the time of their diagnosis.

To develop the AI/ML model, a cohort of transthyretin amyloidosis patients with cardiac manifestation (or ATTR-CM), a subtype of amyloidosis, was selected. The eligibility criteria was built that used ICD diagnosis code and medication records. Patients who have been diagnosed with cardiac amyloidosis were included, whereas patients with light chain amyloidosis, monoclonal gammopathy, multiple myeloma, or other conditions, and patients receiving chemotherapy for plasma cell disease were excluded. About 1,700 eligible patients were identified using the eligibility criteria.

The process for risk stratifying ATTR-CM patients using the AI/ML model was as follows. First, a RNN model was built to predict the mortality of ATTR-CM patients within 2 years or 5 years of diagnosis. Then the model was trained on 80% of the ATTR-CM patient cohort and evaluated on the other 20% of the cohort. There was no patient overlap between the training set and the test set.

Figure 21:
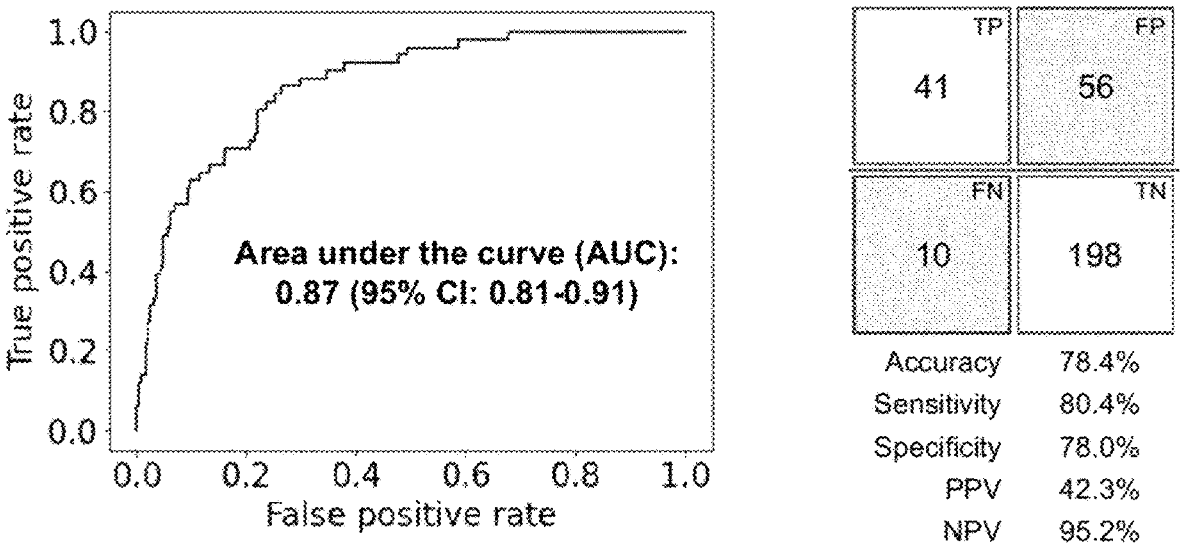
FIG. 21 illustrates the two-year mortality of ATTR-CM patients predicted by an AI/ML model.

FIG. 21 illustrates the two-year mortality of ATTR-CM patients predicted by the AI/ML model. As shown, the AI/ML model was able to predict two-year mortality for ATTR-CM patients, with an area under the curve (AUC) value of 0.87 and an overall accuracy of about 78.4%.

Figure 22:
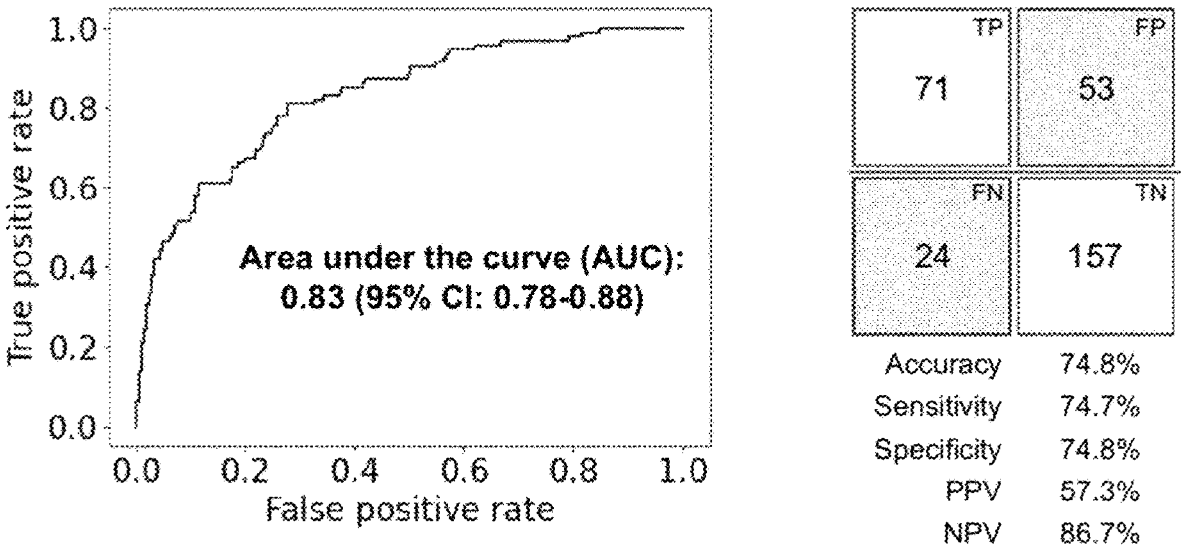
FIG. 22 illustrates the five-year mortality of ATTR-CM patients predicted by an AI/ML model.

FIG. 22 illustrates the five-year mortality of ATTR-CM patients predicted by the AI/ML model. The AI/ML model was able to predict a five-year mortality, with an AUC value of 0.83 and an overall accuracy of 74.8%. It is expected that the performance of the AI/ML model may further be improved as we continue integrating more features and data into the AI/ML algorithms.

Figure 23A:
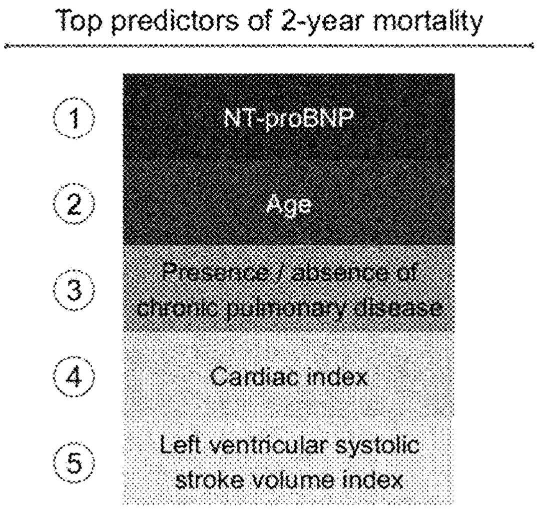
FIG. 23A shows top predictors (features with most importance) of two-year mortality.
Figure 23B:
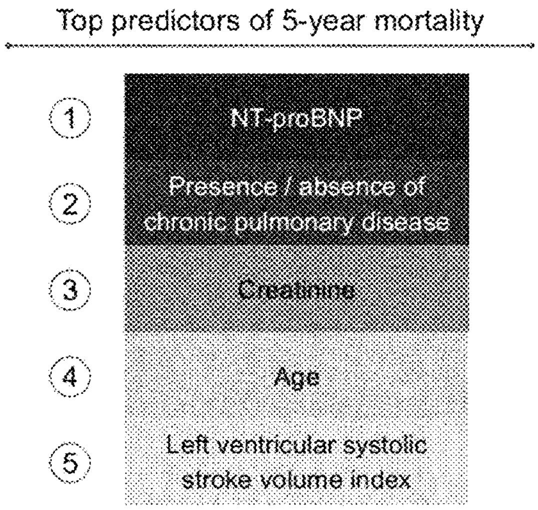
FIG. 23B shows top predictors (features with most importance) of five-year mortality.

A sensitivity analysis was performed to rank feature importance for the AI/ML model prediction. FIGS. 23A and 23B show top predictors (features with most importance) of two-year mortality and five-year mortality, respectively. The top five predictors for two-year mortality were NT-proBNP, age, presence/absence of chronic pulmonary disease, cardiac index, and left ventricular systolic stroke volume index. The top five predictors for five-year mortality were NT-proBNP, presence/absence of chronic pulmonary disease, creatinine, age, and left ventricular systolic stroke volume index.

Example 9: Use of Machine Learning for Early Recognition of Clinical Trajectories and Risk Stratification of Acute Decompensated Heart Failure Patients Patients hospitalized with acute decompensated heart failure (ADHF) have different clinical trajectories during hospitalization [1], which impacts length of stay and risk of readmission. Early recognition of in-hospital trajectories, especially those not responding to treatment, in the hospital course may be crucial to achieve successful decongestion and improve outcomes. While resolution of symptoms and signs, weight loss, decrease in natriuretic peptides, hemoconcentration, and other biomarkers have been used to delineate clinical trajectories, we selected hemoconcentration as a surrogate for decongestion and clinical improvement, because it is one of the objective variables that has been associated with favorable outcomes in prior studies [2-4]. Using systems and methods of the present disclosure, an artificial intelligence (AI) model was developed to accurately predict a patient's in-hospital trajectory delineated by hemoconcentration within 48 hours of admission.

We defined hemoconcentration as an increase in hemoglobin level from admission to discharge during ADHF hospitalization [2]. Although other measures such as albumin or hematocrit have also been used to define hemoconcentration, due to unavailability of repeat albumin levels for most patients, we used hemoglobin [2-4]. The first hemoglobin value collected within the first 48 hours of admission was defined as the "admission hemoglobin"; the last lab collected between Day 4 (96 hours) of hospitalization and date of discharge was defined as the "discharge hemoglobin." A patient with an increase in hemoglobin at discharge relative to the admission hemoglobin was considered to have "hemoconcentration"; those with no increase or a decrease were classified as "no-hemoconcentration". Hemoconcentration achieved by discharge was accepted as a marker of successful decongestion.

This study utilized de-identified clinical data from patients admitted at a multi-site health system, which is a major urban quaternary care center. The data included demographics, laboratory values, vital signs, body weight, medication administration data, and diagnosis codes, obtained from inpatient admission encounters. The clinical data was formulated as a time-series. A recurrent neural network (RNN) model to learn features from clinical variables and diuretic regimens available in the first 48 hours of admission was built to predict whether a patient may have hemoconcentration (increased hemoglobin) at discharge. Machine learning (ML) algorithms were developed to train the RNN model and by using variables during the first 48 hours of hospitalization to predict whether the patient is in a trajectory to develop successful hemoconcentration, as illustrated in FIG. 25.

FIG. 25 shows in Panel 1 an example of a recurrent neural network model that predicts hemoconcentration early based on clinical data available in the first 48 hours of hospital admission (e.g., by Day 2 of the hospitalization). Panel 2A shows association of AI-predicted hemoconcentration with out-of-hospital mortality; Panel 2B shows association of observed discharge hemoconcentration with out-of-hospital mortality.

Of the available ~200,000 patients' hospitalization records, ~4,400 patients (about 70% of the total ADHF patients) and their associated ~6,700 ADHF admissions had both admission and discharge hemoglobin levels available. In these patients, the average length of stay was 8.4±5 days. To evaluate the utility of the AI model to phenotype patients into a "hemoconcentration" group or a "no-hemoconcentration" group, The ADHF admission records were randomly split into training (~50% of the patients, n=2,204) and test (~50% of the patients, n=2,260) sets. There was no patient overlap between the training and test sets. The RNN model was pre-trained on the data from all patients who were not in the test set. Then the RNN model was fine-tuned (trained on a lower learning rate) on the training set and evaluated on the test set in predicting whether a patient may have hemoconcentration.

By Day 2, the AI model predicted those who may have hemoconcentration at discharge with an Area Under the Curve (AUC) of 0.70 (95% CI: 0.68-0.72) (FIG. 25). We compared the outcomes of the two patient groups (predicted hemoconcentration vs. no-hemoconcentration by the AI model) in the test set, shown in FIG. 25. The clinical features included in the AI model that were most predictive of hemoconcentration were admission hemoglobin, presence of malignancy, sodium, age, and presence of renal disease. The AI prediction of hemoconcentration during the first 2 days of hospitalization was associated with lower out-of-hospital mortality. Consistent with prior findings, hemoconcentration at discharge was also associated with out-of-hospital mortality [2-4].

This study demonstrated the potential of utilizing AI to risk stratify and predict clinical trajectories of ADHF patients within the first two days of hospitalization to determine those patients who will and will not have hemoconcentration at the time of discharge. Our AI model can predict discharge hemoconcentration early based on admission data, such that by Day 2, a predicted trajectory and associated out-of-hospital mortality can be defined based on factors such as the patient's baseline health status and current treatment regimen.

Machine learning can help unmask trajectories of patients before they become clinically recognized and reveal novel phenotypes that can enable clinicians to predict patient response to treatment and adjust interventions accordingly. Machine learning models may be trained to an extent such that, e.g., a correlation between AI predicted trajectory groups and 30-day mortality reaches statistical significance. Hemoconcentration represents a potentially addressable but surrogate outcome in heart failure. Other surrogates and endpoints may be investigated to delineate clinical trajectories. Randomized controlled studies may be performed to validate the utility of AI algorithm-assisted care versus usual care, which may be beneficial to differentiate patients who may be safely discharged versus those who may need rapid escalation of therapies and/or longer hospitalization.

REFERENCES

1. Hollenberg, Steven M., et al. "2019 ACC expert consensus decision pathway on risk assessment, management, and clinical trajectory of patients hospitalized with heart failure: a report of the American College of Cardiology Solution Set Oversight Committee." Journal of the American College of Cardiology 74.15 (2019): 1966-2011 is incorporated by reference herein in its entirety.
2. van der Meer, Peter, et al. "The predictive value of short-term changes in hemoglobin concentration in patients presenting with acute decompensated heart failure." Journal of the American College of Cardiology 61.19 (2013): 1973-1981 is incorporated by reference herein in its entirety.
3. Testani, Jeffrey M., et al. "Timing of hemoconcentration during treatment of acute decompensated heart failure and subsequent survival: importance of sustained decongestion." Journal of the American College of Cardiology 62.6 (2013): 516-524 is incorporated by reference herein in its entirety.
4. Greene, Stephen J., et al. "Haemoconcentration, renal function, and post-discharge outcomes among patients hospitalized for heart failure with reduced ejection fraction: insights from the EVEREST trial." European journal of heart failure 15.12 (2013): 1401-1411 is incorporated by reference herein in its entirety.
5. Johnson, Alistair E W, et al. "MIMIC-IV, a freely accessible electronic health record dataset." Scientific data 10.1 (2023): 1 is incorporated by reference herein in its entirety.

Example 10: Mortality Prediction and Risk Factors in Patients Diagnosed with Transthyretin Amyloid Cardiomyopathy Using Machine Learning Transthyretin stabilizing therapy may be more effective in some ATTR-CM patients than the others, and the reduction in all-cause mortality may occur only after approximately 18 months of treatment, indicating that the patients with more advanced disease progression may be less likely to benefit from the stabilizers. To differentiate the risk levels of ATTR-CM patients and determine their risk factors, systems and methods of the present disclosure utilized machine learning to predict mortality of ATTR-CM patients at the time of their diagnosis, and feature importance was ranked in the AI risk stratification model.

This study included patients diagnosed with ATTR-CM at a multi-site health system that spans the U.S. Midwest, Southwest, and Southeast. Clinical features around the time of diagnosis were included as input for the AI model to predict mortality. We randomly split the patients into training (80%) and test (20%) sets. We trained a recurrent neural network model based on the clinical data within 6 months before and 1 year after diagnosis to predict 2-year and 5-year mortality post diagnosis. We calculated the AUC of the AI model evaluated on the test set and used sensitivity analysis to rank the features that are most predictive of mortality.

We extracted 1,727 ATTR-CM patient records, their 2-year outcomes (deceased within 2 years, n=259, age at diagnosis, 74±13 years; survived, n=1,427, age, 68±13 years; uncertain/right-censored, n=41, age, 73±15 years), and their 5-year outcomes (deceased within 5 years, n=504, age at diagnosis, 74±13 years; survived, n=1,023, age, 66±12 years; uncertain/right-censored, n=200, age, 71±14 years). The AI model achieved an AUC of 0.87 (95% CI, 0.81-0.91) in predicting 2-year mortality and an AUC of 0.83 (95% CI, 0.78-0.88) in predicting 5-year mortality.

Sensitivity analysis revealed that the clinical features used in the AI model that were most predictive of 2-year mortality were NT-proBNP, age, presence of chronic pulmonary disease, cardiac index, and left ventricular systolic stroke volume index. Those most predictive of 5-year mortality were NT-proBNP, presence of chronic pulmonary disease, creatinine, age, left ventricular systolic stroke volume index.

An AI model utilizing clinical variables in ATTR-CM patients around the time of diagnosis can accurately predict all-cause mortality. This study demonstrates that trained AI algorithms can rigorously determine which patients are at higher risk for poor outcomes. The explainable AI may further reveal novel phenotypes of patients.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method of treating a no-hemoconcentration subject at risk of a cardiovascular, metabolic, or renal syndrome, disease, or disorder, or heart failure, the method comprising:

(a) receiving, by a computing system comprising at least a processor and a memory, a dataset comprising a set of clinical health data of a no hemoconcentration subject, the set of clinical health data including at least one parameter selected from the group consisting of: B-type natriuretic peptide (BNP), N-terminal (NT)-pro hormone BNP (NT-proBNP), creatinine, a hemoconcentration marker, potassium, troponin, body weight, ejection fraction (EF), estimated glomerular filtration rate (eGFR), medication history, and vital sign measurements or a combination thereof;

(b) transforming, by the computing system, the dataset into a vector using a predefined data processing sequence stored in the memory;

(c) processing, by the computing system, the dataset transformed into the vector containing the set of clinical health data of the subject using a trained machine learning model configured to minimize a loss function, wherein the training data contains inputs including subject numerical clinical data correlated to outputs containing subject outcomes;

(d) applying, by the computing system, the dataset transformed into the vector as input to the trained machine learning model, wherein the trained machine learning model is configured to generate an output containing a treatment recommendation that the subject requires an increased dose of a diuretic therapy;

(e) generating, by the computing system, the treatment recommendation of the dataset containing the set of clinical health data of the no hemoconcentration subject, wherein the treatment recommendation identifies an adjustment to the dose of a diuretic therapy for the no hemoconcentration subject with an area under the curve of 0.70 and greater, and wherein the diuretic therapy is a loop diuretic or a thiazide diuretic;

(f) outputting, by the computing system, a treatment recommendation, the recommendation comprising increasing the dose of the loop diuretic or the thiazide diuretic for the no hemoconcentration subject with an area under the curve of 0.70 and greater; and (g) administering the increased dose of the loop diuretic or the thiazide diuretic to the no hemoconcentration subject to mitigate a predicted adverse clinical outcome.

2. The method of claim 1, wherein determining the treatment recommendation of the no hemoconcentration subject comprises determining a risk score or likelihood of the subject for being readmitted to the hospital within 30 days of discharge.

3. The method of claim 2, wherein determining the treatment recommendation of the no hemoconcentration subject comprises a decision about patient care selected from the group consisting of delaying or expediting discharge and adjusting a medical therapy as a function of the comparison of the risk score to the threshold.

4. The method of claim 1, wherein determining the treatment recommendation of the no hemoconcentration subject comprises determining a progression or regression of the heart failure.

5. The method of claim 1, wherein determining the treatment recommendation of the no hemoconcentration subject comprises generating a set of feature importance values of at least a subset of the set of clinical health data.

6. The method of claim 5, further comprising ranking the at least a subset or generating a visualization based at least in part on the set of feature importance values.

7. The method of claim 6, wherein the visualization comprises a saliency map indicative of the set of feature importance values.

8. The method of claim 7, wherein the saliency map is individualized for the subject.

9. The method of claim 7, wherein the saliency map indicates one or more actionable clinical variables from among the set of clinical health data.

10. The method of claim 1, wherein determining the treatment recommendation of the no hemoconcentration subject comprises determining a prediction, a progression, or a regression of an adverse event to the subject, selected from the group consisting of amyloidosis, arrhythmia, atrial fibrillation, diabetes, heart failure, hyperkalemia, hypokalemia, hypertension, hypotension, kidney injury, pulmonary edema, and renal failure, over the future period of time.

11. The method of claim 1, wherein the diuretic therapy is adjusted if there is a change in at least one parameter selected from the group consisting of BNP, NT-proBNP, body weight, creatinine, hemoglobin, hematocrit, albumin, uric acid, or potassium or a combination thereof.

12. The method of claim 1, wherein the treatment recommendation comprises a guideline-directed medical therapy (GDMT) selected from the group consisting of beta blockers; mineralocorticoid receptor antagonists (MRAs), renin-angiotensin-aldosterone system inhibitors (RAASis), angiotensin receptor blockers (ARBs), or angiotensin receptor neprilysin inhibitors (ARNis) or a combination thereof, and wherein the GDMT is adjusted if serum potassium exceeds 5.2 milliequivalents per liter (mEq/L), N-terminal pro b-type natriuretic peptide (NT-proBNP) exceeds 600 picograms per milliliter (pg/mL), or NT-proBNP or BNP decreases by less than 30% in response to treatment over a defined treatment period.

13. The method of claim 1, wherein the trained machine learning algorithm is selected from the group consisting of a recurrent neural network (RNN) and a convolutional neural network (CNN).

14. The method of claim 1, wherein adjusting the dose of the diuretic therapy further comprises adjusting at least one diuretic therapy selected from the group consisting of: beta blocker; loop diuretic; mineralocorticoid receptor agonists (MRAs), renin-angiotensin-aldosterone system inhibitors (RAASis), angiotensin receptor blockers (ARBs), angiotensin converting enzyme inhibitors (ACEis), and angiotensin receptor neprilysin inhibitors (ARNis).

15. The method of claim 1, wherein the criterion for increasing the diuretic therapy comprises a potassium level is less than 5.2 Milliequivalents Per Liter (mEq/L).

16. A computer-implemented method of treating a transthyretin amyloidosis with cardiac manifestation (ATTR-CM) subject, the method comprising:

(a) receiving, by a computing system comprising at least a processor and a memory, a dataset comprising a set of clinical health data of a transthyretin amyloidosis with cardiac manifestation (ATTR-CM) subject, the clinical health data including at least one parameter selected from the group consisting of B-type natriuretic peptide (BNP), N-terminal (NT)-pro hormone BNP (NT-proBNP), creatinine, a marker, potassium, troponin, body weight, ejection fraction (EF), estimated glomerular filtration rate (eGFR), medication history, vital sign measurements, left ventricular systolic stroke volume index, a presence or an absence of a chronic pulmonary disease of the subject, or age or a combination thereof;

(b) transforming, by the computing system, the dataset into a vector using a predefined data processing sequence stored in the memory;

(c) processing, by the computing system, the dataset using a trained machine learning model configured to minimize a loss function, wherein the training data contains inputs including subject numerical clinical data correlated to outputs containing ATTR-CM assessments;

(d) applying, by the computing system, the dataset transformed into the vector as input to the trained machine learning model, wherein the trained machine learning model is configured to generate an output containing a treatment recommendation that the subject requires an increased dose of a TTR silencer, a TTR stabilizer, or a diuretic therapy;

(e) generating, by the computing system, the treatment recommendation of the dataset containing the set of clinical health data of a transthyretin amyloidosis with cardiac manifestation (ATTR-CM) subject wherein the treatment recommendation identifies an increase to the dose of the TTR silencer, the TTR stabilizer, or the diuretic therapy when a B-type natriuretic peptide (BNP) is greater than 600 picograms per milliliter;

(f) outputting, by the computing system, the treatment recommendation wherein the treatment recommendation comprises increasing the dose of the TTR silencer, the TTR stabilizer, or the diuretic therapy when the B-type natriuretic peptide (BNP) is greater than 600 picograms per milliliter adjusting a medical therapy of the subject to mitigate a predictive ATTR CM assessment risk; and (g) administering the increased dose of the TTR silencer, the TTR stabilizer, or the diuretic therapy when the B-type natriuretic peptide (BNP) is greater than 600 picograms per milliliter to the transthyretin amyloidosis with cardiac manifestation (ATTR-CM) subject to mitigate a clinical outcome.

17. The method of claim 16, wherein determining the treatment recommendation of the ATTR-CM subject comprises determining a risk score or likelihood of the subject for being readmitted to the hospital within 30 days of discharge.

18. The method of claim 17, wherein determining the treatment recommendation of the-ATTR-CM subject comprises, making a decision about patient care selected from the group consisting of delaying or expediting discharge and adjusting a medical therapy as a function of the comparison of the risk score to the threshold.

19. The method of claim 16, wherein determining the treatment recommendation of the ATTR-CM subject comprises determining a progression or regression of the ATTR-CM subject.

20. The method of claim 16, wherein determining the treatment recommendation of the ATTR-CM subject comprises generating a set of feature importance values of at least a subset of the set of clinical health data.

21. The method of claim 20, further comprising ranking the subset or generating a visualization based at least in part on the set of feature importance values.

22. The method of claim 16, wherein determining the treatment recommendation of ATTR-CM subject comprises determining a response of the ATTR CM subject to a medical therapy.

23. The method of claim 16, wherein the treatment recommendation further comprises increasing the dose of the TTR silencer, the TTR stabilizer, or the diuretic therapy when a potassium level is less than 5.2 Milliequivalents Per Liter (mEq/L).

* * * * *